(12) United States Patent
Kim et al.

(10) Patent No.: US 7,495,767 B2
(45) Date of Patent: Feb. 24, 2009

(54) DIGITAL OPTICAL METHOD (DOM™) AND SYSTEM FOR DETERMINING OPACITY

(75) Inventors: Byung J. Kim, Champaign, IL (US); Mark J. Rood, Champaign, IL (US); Ke Du, Urbana, IL (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 338 days.

(21) Appl. No.: 11/407,216

(22) Filed: Apr. 20, 2006

(65) Prior Publication Data

US 2007/0247629 A1 Oct. 25, 2007

(51) Int. Cl.
*G01N 21/00* (2006.01)

(52) U.S. Cl. ............... 356/438; 356/436; 356/437; 348/241; 348/246

(58) Field of Classification Search ......... 356/436–438; 382/224–225, 165, 133, 180, 275; 348/241–246
See application file for complete search history.

(56) References Cited

U.S. PATENT DOCUMENTS

| | | | |
|---|---|---|---|
| 3,841,763 A | 10/1974 | Lewis | |
| 4,614,968 A | 9/1986 | Rattman et al. | |
| 5,237,308 A | 8/1993 | Nakamura | |
| 5,512,942 A | 4/1996 | Otsuki | |
| 6,184,792 B1 | 2/2001 | Privalov et al. | |
| 6,335,976 B1 | 1/2002 | Belmares | |
| 6,505,977 B2 * | 1/2003 | Corbin et al. | 396/567 |
| 6,597,799 B1 * | 7/2003 | Pfaff et al. | 382/100 |
| 6,844,818 B2 | 1/2005 | Grech-Cini | |
| 6,937,743 B2 | 8/2005 | Rizotti et al. | |
| 7,295,233 B2 * | 11/2007 | Steinberg et al. | 348/241 |

OTHER PUBLICATIONS

Du, Ke, et al., Field Evaluation of Digitical Optical Method to Quantify the Visual Opacity of Plumes, J. Air & Waste Manage. Assoc., 57:836-844, 2007.

(Continued)

*Primary Examiner*—L. G Lauchman
*Assistant Examiner*—Iyabo S Alli
(74) *Attorney, Agent, or Firm*—Earl H. Baugher, Jr.

(57) ABSTRACT

Photography is employed to objectively quantify opacity of fluids such as smoke plumes and dust via a method termed the Digital Optical Method (DOM™). The DOM™ quantifies the ratio of radiance values by means of a camera response curve obtained using objective measures. The radiance ratios are then used to calculate opacity of target fluids such as smoke plumes. The DOM™ quantifies opacity during both daytime and nighttime conditions with a much broader range of subject types, e.g., white, gray and black smoke plumes, and environmental conditions, e.g., non-blue-sky, building, and mountain backgrounds, than existing systems while not requiring human interpretation for any application. In one embodiment, the DOM™ quantifies opacity from digital photos using a pre-designed algorithm and an inexpensive digital camera. Very little training is needed to implement the DOM™ and it yields consistent objective quantitative results, while providing a permanent photographic record easily digitally archived.

49 Claims, 14 Drawing Sheets

OTHER PUBLICATIONS

Du, Ke, et al., Quantification of Plume Opacity by Digital Photography, Environ. Sci. Technol., 41, 928-935, 2007.

Du, Ke, Optical Remote Sensing of Airborne Particulate Matter to Quantify Opacity and Mass Emissions, Abstract, Dissertion for PhD at University of Illinois, 2007.

Du, Ke, et al., Field Testing of the Digital Opacity Method to Quantify Plume Opacity During Nighttime, 99th Annual Mtng of Air & Waste Manage. Assoc., No. 1278, p. 15, 2006.

Du, Ke, et al., Evaluation of Digital Image Method to Quantify Opacity of Stationary Source Plumes, 97th Annual Mtng of Air & Waste Manage. Assoc., No. 64, p. 13, 2004.

* cited by examiner

DIGITAL OPTICAL METHOD (DOM™) AND SYSTEM FOR DETERMINING OPACITY

STATEMENT OF GOVERNMENT INTEREST

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees. Please contact Bea Shahin at 217 373-7234 or Phillip Stewart at 601 634-4113.

BACKGROUND

A measurement of opacity is employed in a standard used by the U.S. Environmental Protection Agency (USEPA) for visible emissions. Opacity is defined as the fraction (usually expressed as a percentage) of a light beam, which is in its passage through a smoke plume (or any other attenuating medium), and is removed from that beam by absorption and/or scattering. P. Lilienfeld et al, *Passive Remote Smoke Plume Opacity Sensing: A Technique*, Applied Optics, Vol. 20, No. 5, 800-806, 1981. It can be mathematically defined as 100% minus the percentage of the transmitted light radiance to the initial light radiance. The existing methods for monitoring opacity include Method 9 of the USEPA (*USEPA Visual Determination of the Opacity of Emissions from Stationary Sources*, 60 CFR, App. A. (7-1-92 Edition), 849-855, 1992), in-stack transmissometer (Conner, W. D. and H. B. McElhoe, *Comparison of Opacity Measurements by Trained Observer and In-Stack Transmissometer*, Journal of the Air Pollution Control Association, Vol. 32, No. 9, 943-946, 1982), Light Detection and Ranging (LIDAR) (60 CFR, App. A, *Alternate Method 1—Determination of the Opacity of Emissions from Stationary Sources Remotely by LIDAR*, 855-873, 1992) and the Optical Digital Environmental Compliance System (ODECS) (aka DOCS) (Stretch, J. P. and B. Pfaff, Summary Report for the Joint NASA, Space Dynamics Laboratory, SCIENTECH, Inc., *Remote Sensing Project on an Optical Digital Environmental Compliance System (ODECS)*, 1999).

USEPA Method 9 requires a certified human observer to quantify plume opacity in the ambient environment immediately outside of the source. This method introduces human bias and involves extensive labor costs to train personnel and implement the method. 60 CFR (1992). USEPA Method 9 requires that an observer have an individual opacity error, $d_i$, of less than 15% and an average absolute opacity error, $\bar{d}$, of less than 7.5% for all fifty black and white plumes evaluated during a particular test. Passing this test certifies the observer for six months. The individual opacity error, $d_i$, is the absolute error between an individual opacity value, $0_{2,i}$, as measured by the in-stack transmissometer, and the observed opacity value, $0_{1,i}$, by the human or digital camera as described by:

$$d_i = |0_{1,i} - 0_{2,i}| \tag{1}$$

where subscript i represents each corresponding measurement and observation for all fifty tests. The average absolute opacity error, $\bar{d}$, is defined as:

$$\bar{d} = \frac{\sum_{i=1}^{n} |d_i|}{n} = \frac{1}{n} \cdot \sum_{i=1}^{n} |0_{1,i} - 0_{2,i}| \tag{2}$$

where n is the number of paired observations.

The in-stack transmissometer method quantifies plume opacity within the exhaust stack of the source. The system requires installation and maintenance for each source. A transmissometer may be purchased for $7,000-$12,000. Conner and McElhoe (1982).

LIDAR is used as a research instrument to quantify the opacity of the atmosphere and is very expensive, e.g., at least tens of thousands of dollars. Furthermore, since LIDAR measurements inherently yield positive error for plume transmittance, LIDAR underestimates the opacity of plumes. CFR (1992). Cook, C. S., et al., *Remote Measurement of Smoke Plume Transmittance Using LIDAR*, Applied Optics, Vol. 11, No. 8, 209-215, 1972. Additionally, transmissometers and LIDARs do not provide records, e.g., photographs that may be useful for demonstrations and legal actions.

Use of photography to quantify ambient visual range and plume opacity is a promising method to lower costs, improve accuracy and precision, reduce subjectivity, and provide a photograph as a record of the observation. Photographic techniques have been used in visibility studies during the past thirty years as described below. The fundamental relationship between visual range, contrast, and the scattering coefficient was initially derived more than eighty years ago. Koschmieder, H., *Beitr. Phys. freien Atm.* 12, 171-181, 1924 as cited by Hoffer, T. E. et al., *The Science of the Total Environment* 23, 293-304, 1982. Then, Barber and Larson developed a relationship between the visual range (defined as the distance at which a large black object just disappears from view) and a backscattering coefficient based on Koschmieder's theory. Barber and Larson, *Appl. Opt.*, 24(21), 3223-3525, 1985.

Visual range of the vista of an ambient environment was quantified using the concept of inherent contrast and film densities, when using a 35 mm camera, black and white film or color film, and a digitizer. Hoffer et al. (1982). These photographs were used to calculate visual range for clear sky conditions. However, factors such as horizon brightness, cloudiness and shadows were not included in the calculations. First principles needed to simulate the effect of uniform haze photographically were described in the early 1980s, and a visibility model was developed based on those principles. Malm, W. C. et al., Journal of the Air Pollution Control Association, 33, 126-129, 1983. Visibility modeling was then tested experimentally in the late 1980s. Larson, S. M. et al., *Environmental Science & Technology*, 22, 629-637, 1988. Also, the atmospheric transmittance and path radiance were determined using two cameras taking pictures for the same scene at different distances (Richard et al., *Environ. Sci. Technol.*, 23, 182-186, 1989) based on the equations described in Malm et al. (1983). Optical measurement of transmission and scattered radiance for a ground-level plume generated by a stationary jet engine was completed with the use of two multi-detector teleradiometers and a 6.1 by 6.1 m contrasting panel located 4.6 m behind the plume. Johnson, C. E. et al., *Transactions of the Air & Waste Management Association*; Mathai, C. V., Ed., 348-362, 1990.

More sophisticated aerosol and radiative transfer models were then developed to simulate visual air quality conditions in the mid-1990's. Molenar, J. V. et al., *Atmospheric Environment*, 28, 1055-1063, 1994. Digital photos were used to characterize visibility in the late 1990's and the results from digital photos were compared with LIDAR measurements. Xie, X. et al., *Chinese Science Bulletin*, 44, 1130-1134, 1999.

The initial use of digital photography to quantify visible plume opacity was described with the Digital Opacity Compliance System (DOCS). Stretch and Pfaff (1999). DOCS is also termed ODECS and is protected by U.S. Pat. No. 6,597,799, to Pfaff et al., *Optical Digital Environment Compliance System*, issued Jul. 22, 2003. The patent provides a method and apparatus for analyzing a digital photograph of an effluent to determine its opacity. A photograph of the effluent is analyzed at the pixel level. Each pixel corresponding to the effluent is identified and the color of each effluent pixel is analyzed to calculate the opacity of that effluent pixel. An opacity value for the entire effluent is extrapolated based on the opacity values of each pixel.

DOCS has used a specific digital camera with software that is installed in the camera. The camera is self-calibrating for clear-sky backgrounds only. To calculate the opacity of a plume, the operator selects an area in the photograph. The area must include a part of the plume to be determined for opacity as well as a portion of the clear-sky background. The performance of DOCS was evaluated at USEPA-approved smoke schools under clear-sky conditions. McFarland, M. J. et al., *Journal of the Air & Waste Management Association*, 53, 724-730, 2003. DOCS was also evaluated in overcast-sky conditions. McFarland, M. J. et al., *Journal of the Air & Waste Management Association*, 54, 296-306, 2004.

DOCS uses a digital camera to quantify plume opacity from a point source but works autonomously, i.e., self-calibrates, only during the day under clear-sky conditions. McFarland et al. (2003). DOCS may quantify plume opacity when the sky is overcast or the background is a building or a mountain. However, the operator needs to provide a color scale from which to estimate the opacity of a 100% opaque plume. Stretch et al. (1999). Clear-sky backgrounds are not typical, especially in low altitude and humid environments such as in the Midwestern U.S. and in marine environments. Also, human bias is introduced for all of those measurements in which a clear-sky background is not available since an operator must choose the color scale for a 100% opaque plume.

What is needed is a method employing an inexpensive digital camera that will yield objective quantitative opacity results for clear-sky, cloudy-sky, and nighttime conditions and provide for efficient storage of results for future use with no need for interpretation by an operator. In select embodiments of the present invention, the Digital Optical Method (DOM™) quantifies the ratio of radiance values by means of a camera response curve obtained using objective measures. The radiance ratios are then used to calculate plume opacity. The DOM™ quantifies the opacity of a subject, such as a plume from a smoke stack, from digital photos using a pre-designed algorithm and an inexpensive and readily available digital camera. Very little training is needed to implement the DOM™ and it yields consistent objective quantitative results, i.e., without need for human interpretation. Moreover, the DOM™ provides a permanent photographic record of the subject.

DETAILED SPECIFICATION

Figure 1:
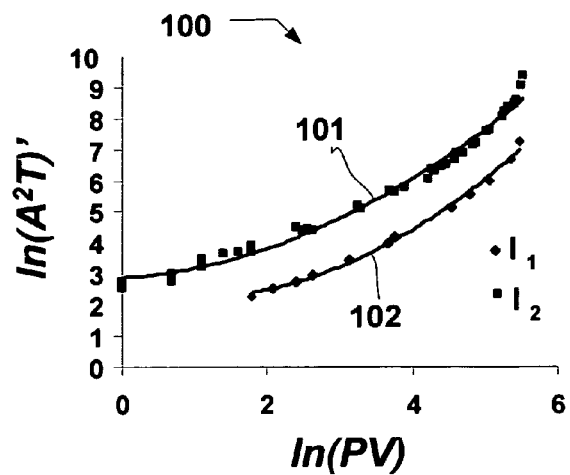
FIG. 1 is a typical plot of data for two different radiance values from which regression analysis permits curves to be constructed from which a digital camera may be calibrated.

Select embodiments of the present invention employ digital photography to objectively quantify opacity via a method termed the Digital Optical Method (DOM™). The DOM™ quantifies opacity with a much broader range of subject types, e.g., white, gray and black smoke plumes, and environmental conditions, e.g., nighttime and non-blue-sky, building, and mountain backgrounds, than existing systems such as ODECS while not requiring human interpretation for any application. For example, by employing an artificial background, the DOM™ is able to quantify opacity for plumes that are gray, i.e., neither black or white.

Select embodiments of the present invention were developed to solve a number of existing problems when monitoring opacity. The first is to remove subjectivity, i.e., human bias, associated with the quantification of opacity when using Method 9 of the USEPA. Select embodiments of the present invention generate digital photographs (graphical images) over a wide range of ambient conditions. These photos are processed to yield objective quantification of opacity for all colors and all natural backgrounds. Further, the DOM™ operates without need for subjective interpretation and is suitable for in-situ and rapid response by facilitating near real-time analysis with results well within the error requirements of USEPA Method 9. This is not possible with any of the existing methods to include: USEPA Method 9, in-stack transmissometers, LIDAR, and ODECS (aka DOCs).

In addition to eliminating subjectivity, select embodiments of the present invention may generate permanent photographic records inexpensively. This is not possible with USEPA Method 9, transmissometer measurements, or LIDAR. Further, while providing accurate measurement of opacity, select embodiments of the present invention significantly reduce the cost of monitoring and determining compliance for both elevated and ground level sources compared to USEPA Method 9, use of in-stack transmissometers, and LIDAR. Finally, select embodiments of the present invention may provide quantitative opacity measurements by employing two distinct methods using the same photograph. This permits objective near real time verification of results when conditions are appropriate for using the contrast or transmission methods of the DOM™.

Select embodiments of the present invention provide a method for obtaining an accurate measure of the opacity of a fluid. In general, the method comprises providing one or more image receiving devices each incorporating one or more light sensitive devices; calibrating the image receiving devices; employing an image receiving device for taking images of the fluid, the images to include one or more backgrounds associated with the fluid; providing one or more algorithms and software to manipulate both the algorithms and data representing the images; providing one or more processors to manipulate the data and run the software; and analyzing the image data using the algorithms and software to obtain an accurate measure of opacity.

In select embodiments of the present invention the fluid is one or more airborne fluids and may comprise effluents selected from: point source effluents, non-point source effluents, exhaust plumes, smoke, dust, and combinations thereof.

In select embodiments of the present invention, the fluid is one or more gases or liquids.

In select embodiments of the present invention, the image receiving device may be one or more cameras, with at least one preferably a digital camera incorporating manual exposure control.

In select embodiments of the present invention, the images are photographs, preferably digital photographs taken in the visible light spectrum.

In select embodiments of the present invention the background may be: naturally occurring backgrounds, man made backgrounds, pre-specified man made backgrounds, and combinations thereof.

In select embodiments of the present invention, the algorithm is represented in a contrast model establishing one or more ratios of the received radiances of a first pre-specified background behind the fluid to one or more ratios of received radiances of a second pre-specified background beside the fluid, such that the relative positions of the first and second background materials are with respect to the orientation of the aperture of the image receiving device to the fluid, and such that each of the first and second pre-specified backgrounds have one or more of each of a light-colored and a contrasting dark-colored portion, and such that the background may be wholly natural, wholly man made, and combinations thereof, but mostly uniform.

In select embodiments of the present invention the algorithm represents a transmission model establishing one or more ratios of the received radiance of a background having contrast to the fluid to the received radiance of the background that is beside the fluid, such that portions of the background are at least behind and beside said fluid, and such that the background may be wholly natural, wholly man made, and combinations thereof, but mostly uniform.

In select embodiments of the present invention, the software may be commercial-off-the-shelf (COTS) software, commercially available software, application specific software, custom software, shareware, freeware, and the like, and combinations thereof.

In select embodiments of the present invention, the processors may be personal computers, computers, application specific integrated circuits (ASICs), personal digital assistants (PDAs), laptop computers, digital processors, and the like, and combinations thereof.

In select embodiments of the present invention, the image receiving device is calibrated by obtaining a response curve for it, such that the response curve describes the relationship between pixel values in the image obtained by the image receiving device and the exposure received by the light sensitive device incorporated in the image receiving device, and such that the response curve provides a means to obtain from the pixel values the ratio of received radiance values, $I_1/I_2$, of any two pixels of an image, where $I_1$ and $I_2$ are radiance values for the two pixels, respectively, and such that the response curve is used to obtain $I_1/I_2$ from the image.

In select embodiments of the present invention, the response curve is empirically obtained for one or more types of digital cameras, each having a minimum resolution of approximately one megapixel and employing a charge coupled device (CCD). In general, the response curve is obtained by fixing the aperture of the camera at a pre-specified value, preferably F8, to minimize vignetting; setting the sensitivity factor of the CCD at a pre-specified value, preferably ISO 100, such that exposure is dependent upon only two variables, scene radiance, I, and exposure time, T; selecting a homogeneous background, such that an average of pixel values, $PV_{AVE}$, may be used to represent mean scene radiance, and such that homogeneous incident radiance is assumed over the area of the aperture of the camera; taking photographs of the homogeneous background, such that photographs are taken during a pre-specified short time period, each with different exposure times, and such that lighting conditions are stable to ensure constant scene radiance; cropping each photograph to employ the center of each; determining $PV_{AVE}$ from the cropped photographs; multiplying the square of the aperture diameter, A, by the exposure time, T, for each cropped photograph; plotting ln(PV) versus $$\ln\left(\frac{A^2 T}{A_{min}^2 T_{min}}\right),$$

where $A_{min}$ is the minimum aperture diameter (aperture setting) and $T_{min}$ is the minimum exposure time used for the set of photographs; determining and plotting as a first curve a first set of data for ln(PV) vs. ln($A^2T$)' from the digital images taken at a first level of radiance yielding incidence value, $I_1$; determining and plotting as a second curve, approximately parallel to the first curve, a second set of data for ln(PV) vs. ln($A^2T$)' from the digital images taken at a second level of radiance yielding incidence value, $I_2$, such that the relationships described by ln(PV) vs. ln($A^2T$)' and obtained at different radiance values are approximately parallel to each other, each point being obtained from one digital photograph of the homogeneous background, and such that the first and second curves are polynomial regression lines for the two sets of data, and such that a constant vertical distance between the two curves represents the constant ratio of the radiance values, $\ln(I_1/I_2)$.

In select embodiments of the present invention, types of digital cameras having only automated exposure control may be calibrated by first calibrating a digital camera having manual exposure control and correlating photographs taken with the camera having manual exposure control to photographs taken with the camera having automated exposure control.

In select embodiments of the present invention, the method further comprises establishing the horizontal distance between the camera and the fluid to be between about three times the height of the fluid above the height of the camera and up to 1 Km (based on an opacity of 4.2% for a path length of 1 Km); adjusting the view in the viewfinder of the camera such that the width of the fluid being measure for opacity is between about 1/10 and about 1/20 of the total width of the image in the viewfinder; and, when photographing outside, positioning the aperture of the camera such that the sun is somewhere within a maximum of approximately a 200° sector behind the aperture for all photographs.

In select embodiments of the present invention, the fluid is a smoke plume from a smoke stack and the method further comprises selecting a sampling area to be about one diameter of the smoke stack above the top of the smoke stack.

In select embodiments of the present invention, a system obtains an accurate measure of the opacity of a fluid. In general, the system comprises one or more calibrated image receiving devices; images of the fluid to include one or more backgrounds associated with the fluid as taken with the image receiving devices; one or more processors for manipulating data related to the images; and software suitable for implementing one or more algorithms for analyzing data to obtain an accurate measure of opacity.

In select embodiments of the present invention, the system measures opacity of one or more airborne fluids, preferably airborne effluents such as point source effluents, non-point source effluents, exhaust plumes, smoke, dust, and the like, and combinations thereof. In select embodiments of the present invention, the system measures opacity of one or more liquids.

In select embodiments of the present invention, the system employs one or more cameras, preferably digital cameras at least one of which incorporates manual exposure control, as the imaging receiving device.

In select embodiments of the present invention, the system processes images that are photographs, preferably digital photographs taken in the visible spectrum.

In select embodiments of the present invention, the system employs backgrounds such as naturally occurring backgrounds, man made backgrounds, pre-specified man made backgrounds, and the like, and combinations thereof.

In select embodiments of the present invention, the system uses software such as commercial-off-the-shelf (COTS) software, commercially available software, application specific software, custom software, shareware, freeware, and the like, and combinations thereof.

In select embodiments of the present invention, the system employs processors such as personal computers, computers, application specific integrated circuits (ASICs), personal digital assistants (PDAs), laptop computers, digital processors, and the like, and combinations thereof.

In select embodiments of the present invention, an instrument package is employed for receiving images suitable to be analyzed to provide an accurate measure of opacity of a fluid. The package comprises one or more calibrated image receiving devices. In select embodiments of the present invention, the instrument package is employed to measure opacity of one or more airborne fluids, preferably airborne effluents such as point source effluents, non-point source effluents, exhaust plumes, smoke, dust, and the like, and combinations thereof. In select embodiments of the present invention, the instrument package measures opacity of one or more liquids.

In select embodiments of the present invention, the instrument package employs one or more cameras as the image receiving device, preferably digital cameras, and most preferably at least one digital camera incorporating manual exposure control for obtaining images as digital photographs taken in the visible light spectrum.

In select embodiments of the present invention, the instrument package contains one or more processors such as personal computers, computers, application specific integrated circuits (ASICs), personal digital assistants (PDAs), laptop computers, digital processors, and the like, and combinations thereof.

In select embodiments of the present invention, the instrument package contains software such as commercial-off-the-shelf (COTS) software, commercially available software, application specific software, custom software, shareware, freeware, and the like, and combinations thereof.

In select embodiments of the present invention, in general a system for obtaining an accurate measure of the opacity of a fluid comprises one or more calibrated means for receiving images; images of said fluid to include one or more backgrounds associated with the fluid, the images obtained with the calibrated means for receiving images; one or more means for processing data; and one or more means for implementing one or more algorithms for analyzing the images.

In select embodiments of the present invention, the calibrated means for receiving images is one or more calibrated digital cameras; the images are digital photographs; the backgrounds are such as naturally occurring backgrounds, man made backgrounds, pre-specified man made backgrounds, and combinations thereof; the means for processing data are such as personal computers, computers, application specific integrated circuits (ASICs), personal digital assistants (PDAs), laptop computers, digital processors, and the like, and combinations thereof; and the means for implementing the algorithms are such as commercial-off-the-shelf (COTS) software, commercially available software, application specific software, custom software, shareware, freeware, and the like, and combinations thereof.

The theory of operation of the DOM™ is based on using a digital image processing technique based on first principles to obtain a response curve for a digital camera and interpreting the photos with software on a computer, such as a PC. The DOM™ may employ either a contrast or transmission model, or both as a comparison, as described below. The software used with the DOM™ may be based on codes written in commercially available software, such as MATLAB® or VISUAL STUDIO, and the like.

To initially implement the DOM™, the software of the DOM™ is employed with a digital camera that is calibrated to obtain a response curve typically not available from the manufacturer. Calibration consists of a series of photographs of a scene that has stable and uniform radiance, e.g., part of a blue sky or a white wall with diffusive reflection. Kim, B. J. et al. Draft Report for Research Project: *Use of Image-Processing Techniques To Measure Plume Opacities*, ERDC-CERL Technical Report (Final report to be published in 2006). These photos are obtained using a range of exposure times that result in increasing pixel values (PVs) with increasing exposure time. The empirical response curve thus obtained describes the dependence of the PVs on exposure time for the series of photographs. Kim et al. (2006). For a scene with heterogeneous incident radiance, e.g., a smoke plume and its environs, the radiance ratio between any two areas in the digital photo may be determined from the corresponding PVs from the photo and the response curve. In select embodiments of the present invention, optimal camera position is with the sun in a 140° sector (with an allowable maximum of an approximately 200° sector) to the back of the camera, and the line of sight of the camera should be approximately perpendicular to the vertical centerline of the subject, e.g., a rising smoke plume. In select embodiments of the present invention, the horizontal distance between the camera and subject, e.g., a smoke plume from a stack, should be between about three times the height of the subject and up to 1 Km.

In select embodiments of the present invention, when taking photos, the photographer should adjust the distance and zoom so that the width (or diameter) of the subject is between about 1/10 and about 1/20 of the total width of the image in the viewfinder. At least one megapixel is recommended for the resolution of the digital photo. In select embodiments of the present invention, the sampling area for smoke plumes should be about one diameter of the stack above the top of the stack to yield a representative estimate of opacity. In select embodiments of the present invention, an appropriate contrasting background is a flat object with both light and dark surfaces that are diffusive to light, e.g., a panel coated with flat paint. In select embodiments of the present invention, a contrasting background should be located behind the subject, e.g., a smoke plume, and another beside it. One preferable embodiment of an artificial contrasting background is a black and white checkered panel having a surface that has diffusive reflection.

Figure 7:
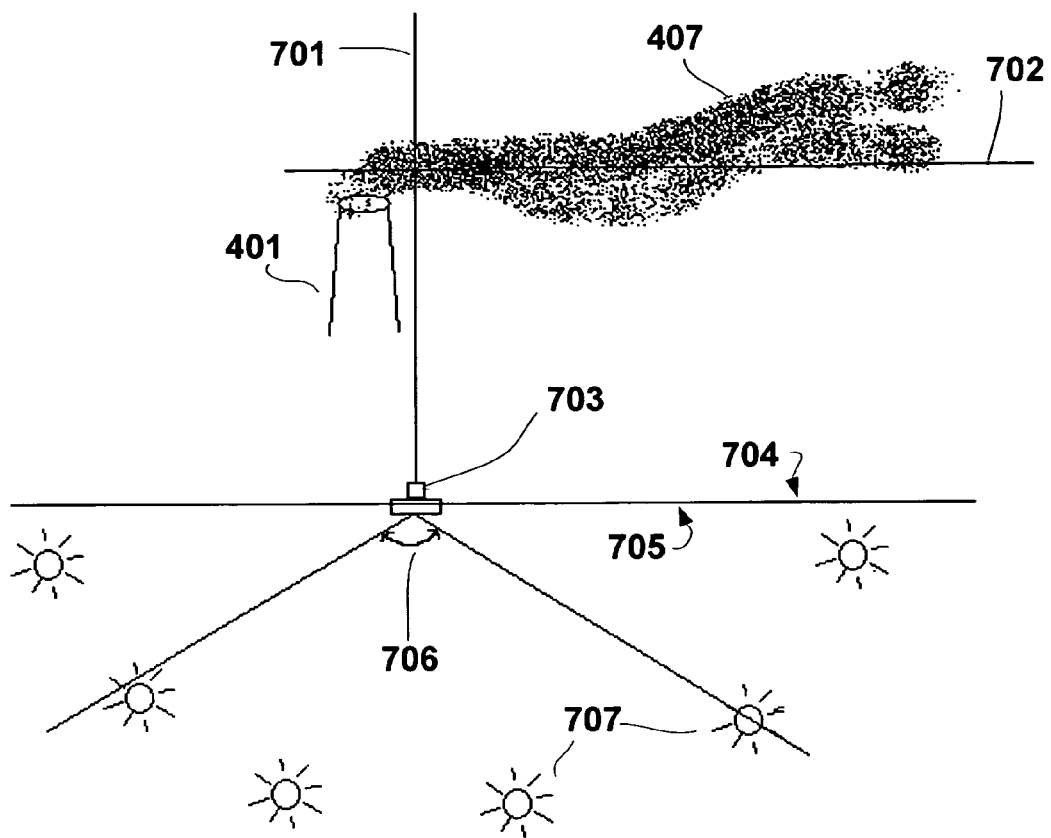
FIG. 7 depicts a camera as used in a first configuration suitable for use with a transmission model that may be employed with select embodiments of the present invention.
Figure 8:
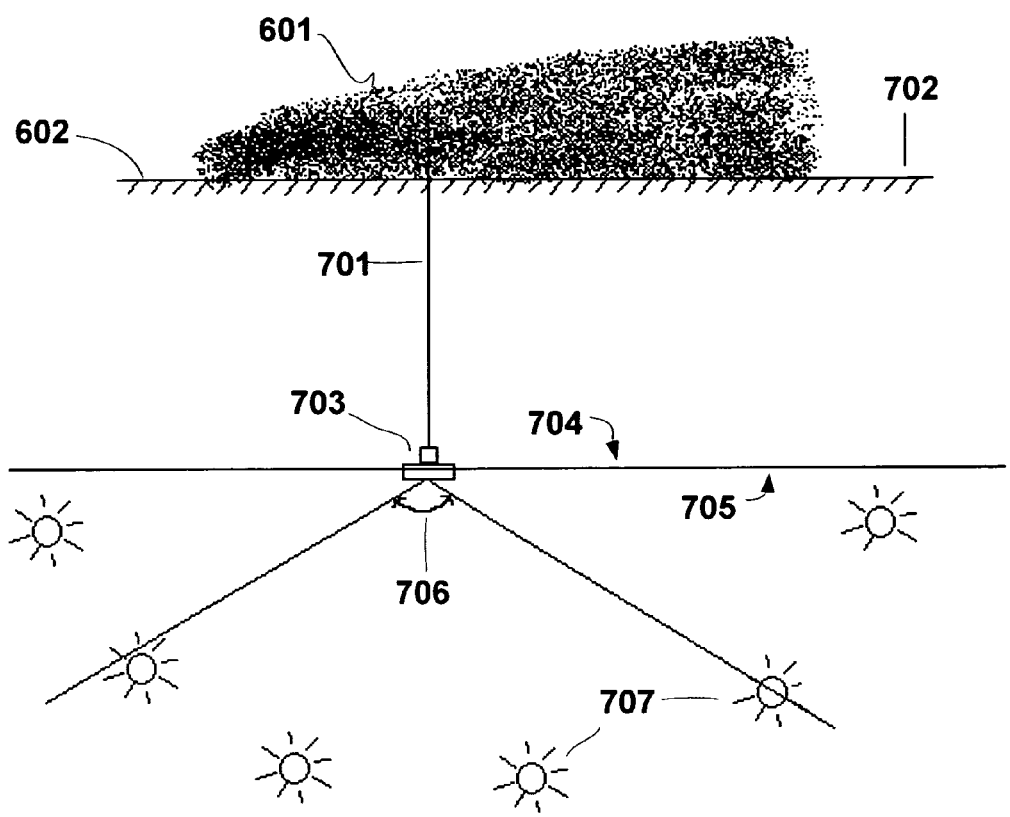
FIG. 8 depicts a camera used in a second configuration that may be used with a transmission model that may be employed with select embodiments of the present invention.

For select embodiments of the present invention, a plan view of the position of the digital camera relative to the plume and sun is illustrated for elevated point and ground-level sources in FIGS. 7 and 8, respectively. The line of sight 701 of the camera should be perpendicular to the plume's centerline 702. However, corrections can be made for conditions when the line of sight 701 for the camera is not perpendicular to the centerline 702 of the plume. Field tests indicate good results with this method as long as the sun 707 is within about an maximum of a 200° azimuth sector to the back 705 of the camera 703. This provides a broader range of available time as compared to Method 9 of the U.S. Environment Protection Agency (USEPA) since Method 9 requires the sun to be located within a 140° sector 706 to the back of the camera 703. EPA (1992).

Refer to FIG. 8. In select embodiments of the present invention the distance between the plume 601 and camera 703 needs to allow for a complete view of the plume 601 and any artificial or natural background (not shown separately) in FIG. 8). For typical ground-level sources, the distance between the camera 703 and plume 601 should be in a recommended practical range of approximately 50-100 m. Refer to FIG. 7 for elevated sources, such as smoke stacks 401. In select embodiments of the present invention the horizontal distance between the camera 703 and the plume 407 (FIG. 7) should be at least about three times the height of the plume 407 above the position of the camera 703.

A response curve describes the relationship between the pixel values (PVs) in a photograph taken by a digital camera and the exposure (E) received by the light sensitive device in the digital camera. This response curve provides a means to obtain the radiance ratio of any two sectors in the scene from the PVs in the corresponding digital photograph. The response curve for a digital camera may be established empirically as described below. Once the camera response curve is determined, the opacity of a subject, such as a plume from a smoke stack, may be quantified according to either contrast or transmission models or both. Detailed operational procedures, such as selection of camera type, camera settings, selection of artificial background, orientation of the camera with respect to the subject, and a description of field test results are also discussed below. In select embodiments of the present invention, initial steps to implement the DOM™ involve camera calibration.

Camera calibration. To calibrate a camera having available a manual mode of setting aperture diameter (A) and exposure time (T), knowledge of the theory of its operation is helpful. Exposure (E) of a charge-coupled device (CCD) sensor in a digital camera is proportional to the aperture area ($\frac{1}{4}\pi A^2$) and exposure time. The exposure that is experienced by a CCD sensor may be expressed as:

$$E = \sum_i E_i \qquad (3)$$
$$= \sum_i F_i \times T \times S_i$$
$$= C' \cdot T \int_S \int I\, dx\, dy$$
$$= C' \times \bar{I} \times \frac{\pi}{4} A^2 T$$

Where:
$F_i$=irradiance received by a pixel;
$S_i$=the area of each pixel;
$C'$=a constant;
I=the scene radiance over the differential area (dxdy) of a pixel;
$\bar{I}$=average scene radiance over the total aperture area, $$\frac{\pi A^2}{4};$$

A=aperture diameter (setting); and
T=exposure time.

It is difficult to measure the exposure of a sensor incorporating a charge-coupled device (CCD) in a digital camera. However, if the incident radiance is constant, then exposure is linearly proportional to the product of aperture area, $$\frac{\pi A^2}{4},$$

and exposure time, T, according to Eqn. (3). To determine this function, first relate ln(E) and ln(PV) as:

$$\ln(E) = \ln\left(C' \cdot \bar{I} \cdot \frac{\pi}{4}\right) + \ln(A^2 T) = g[\ln\overline{PV}] \qquad (4)$$

where $\bar{I}$ is the average incident radiance; $\overline{PV}$ is the average pixel value, and the function g is another version of a camera response curve.

For homogeneous incident radiance, there is a uniform image with the same PVs for all pixels. Therefore, the $\bar{I}$ and $\overline{PV}$ in Eqn. (4) can be replaced by I and PV such that:

$$\ln(E) = \ln\left(C' \cdot I \cdot \frac{\pi}{4}\right) + \ln(A^2 T) = g\ln(PV) \qquad (5)$$

A camera response curve may be used to obtain the radiance ratio, $I_1/I_2$, from a digital image, where $I_1$ and $I_2$ are radiance values for different pixels. For the same photo, the PVs are also the same with constant A and T, resulting in:

$$\frac{I_1}{I_2} = \frac{E_1}{E_2} = e^{(\ln E_1 - \ln E_2)} = e^{[g(\ln PV_1) - g(\ln PV_2)]} \qquad (6)$$

In select embodiments of the present invention, the next step to implement the DOM™ is to empirically obtain a response curve for the type of digital camera to be employed. In select embodiments of the present invention, the aperture of the camera is fixed at a small F-stop, e.g., F8, to minimize any vignetting effect. The CCD sensitivity factor is fixed, e.g., at ISO 100, so that the exposure is dependent only on two variables, scene radiance, I, and exposure time, T. A background is selected to be as homogeneous as possible so that the average of pixel values, $\overline{PV}$, may be used to represent the mean scene radiance. An appropriate background may be a white wall, e.g., a wall painted with flat white paint that insures a diffuse reflection of visible light. With this setup, homogeneous incident radiance may be assumed over the area of the aperture. Photos of the homogeneous background are taken. Multiple photographs of the same scene are taken during the same time period but with different exposure times. That is, photographs are taken over a short time period with stable lighting conditions, to ensure constant scene radiance. For each photograph, the photo is cropped to employ the center of each, ensuring homogeneity of the scene. From this cropped photo, PV is determined. The square of the aperture diameter, A, is then multiplied by the exposure time, T, for each photo. The ln(PV) is then plotted versus $$\ln\left(\frac{A^2 T}{A_{\min}^2 T_{\min}}\right),$$

an example of which is shown in FIG. 1,
where:
$A_{min}$=the minimum aperture size available on the camera;
$T_{min}$=the minimum exposure time for the group of photos (so as to normalize camera exposure during calibration)

Since the aperture is fixed at a minimum setting available on the camera, $$\frac{A^2 T}{A_{\min}^2 T_{\min}} = \frac{T}{T_{\min}} \qquad (7)$$

To solve for $E_i$=f($PV_i$), $$\ln(E_i) = g\ln(PV_i) \qquad (8)$$

must be solved.

For constant and homogenous incident radiance, $$E_i = C''A^2T \quad (9)$$

from Eqn. (3), where $$C'' = C' \cdot \bar{l} \cdot \frac{\pi}{4}.$$

Substitution of $E_i$ into Eqn. (5) yields:

$$\ln(A_2T) = g(\ln PV) - \ln(C'') \quad (10)$$

$A^2T$ may be normalized by $A^2_{min}T_{min}$ so that:

$$(A^2T)' = \frac{A^2T}{A^2_{min}T_{min}} \quad (11)$$

Therefore, $$\ln(A^2T)' = g(\ln PV_i) - \ln(C'') - \ln(A_{min}^2 T_{min}) = g[\ln PV_i] - C''' \quad (12)$$

where $C''' = \ln(C'') + \ln(A_{min}^2 T_{min})$.

One set of data for $\ln(PV)$ vs. $\ln(A^2T)'$ is determined from the digital images taken at a certain level of radiance. Since C''' is a constant, the relationships between $\ln(PV)$ vs. $\ln(A^2T)'$ that are obtained at different radiance values are parallel to each other. Such parallel response 100 is demonstrated in FIG. 1 with experimentally derived values that were obtained at two different incidence values, $I_1$ and $I_2$. Each point was obtained from one digital photo of a homogeneous background. The curve for photos represented by squares 101 was taken under the incident radiance level of $I_1$, and the curve represented by rhombi 102 was taken under the incident radiance level of $I_2$. The curves 101, 102 through the respective points are polynomial regression lines for the two sets of data. The constant vertical distance between the two curves represent the constant ratio of the radiance values, $\ln(I_1/I_2)$.

Figure 2:
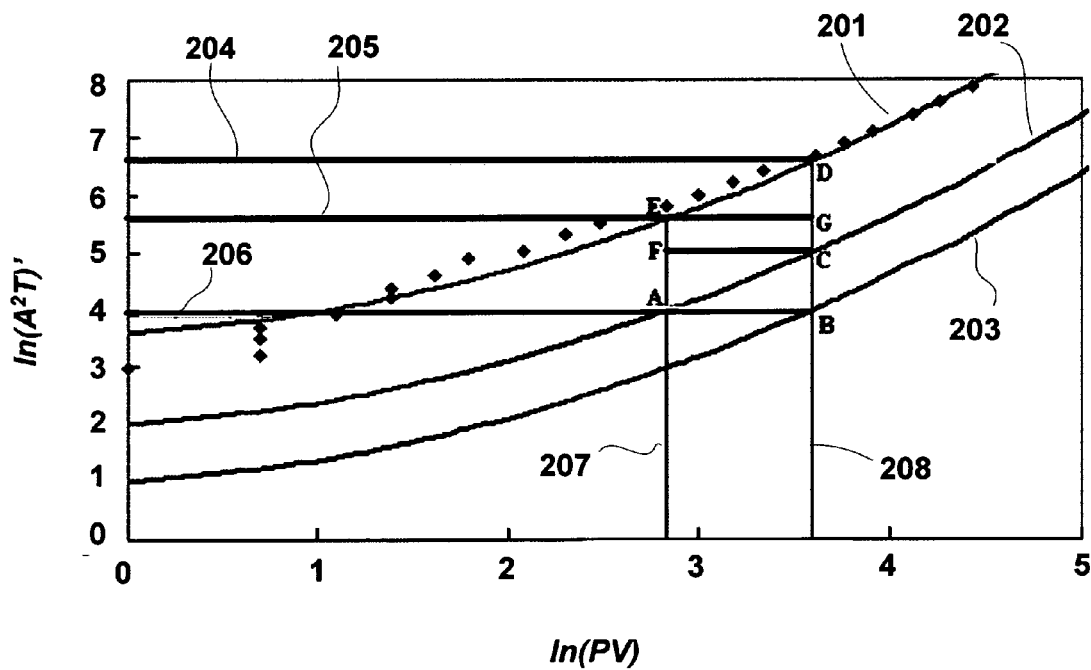
FIG. 2 depicts a calibrated response curve, a response curve at a first radiance and a response curve at a second radiance from which a ratio of the two radiance levels may be determined.

Determining Scene Contrast From Empirical Camera Response Curve. To quantify the scene contrast between any two small areas in the digital image, two sectors of the digital photo are cropped by manually placing digitally generated boxes around the two small areas. These two "boxed" sectors are used to calculate mean pixel values, $PV_{1,AVE}$ and $PV_{2,AVE}$, as described graphically in FIG. 2. The top curve 201 is the calibrated camera response curve. The middle curve 202 is the response curve at a first radiance, $I_1$, and the bottom curve 203 is the response curve at a second radiance, $I_2$. Points A and B represent boxed sectors 1 and 2, respectively, of the sampled photos. Points A and B have the same coordinate value of $\ln(A^2T)'$ since they belong to the same photo. Points A and B also belong to two response curves corresponding to radiance $I_1$ and $I_2$, respectively. The ratio of $I_1$ to $I_2$ is determined geometrically as described below because the middle curve 202 is parallel to the top calibration curve 201, thus $|AE|=|CD|$ and:

$$\ln\left(\frac{I_2}{I_1}\right) = \ln(A^2T)'|_C - \ln(A^{2T})'|_B = |CB| = |AF| \quad (13)$$

EG and FC are straight lines parallel to the abscissa axis, thus $|EF|=|GC|$. Therefore, $$|CB|=|AF|=|AE|-|EF|=|CD|-|GC|=|DG|=\ln(A^2T)'_D - \ln(A^2T)'_E \quad (14)$$

and $$\frac{I_2}{I_1} = e^{\ln(A^2T)_D - \ln(A^2T)_E} \quad (15)$$

$$= e^{[g((\ln PV)_D) - g((\ln PV)_E)]}$$

$$= e^{[g((\ln PV)_2) - g((\ln PV)_1)]}$$

Therefore, the radiance ratio between small areas 1 and 2 is quantified from respective pixel values, PV, when using the response curve of the camera.

The curve 102 describing $I_2$ in FIG. 1 is used to interpolate the results. A polynomial regression is used to obtain the empirical response function. For example, the regression line for the response curve of a CANON POWERSHOT® G3 digital camera is:

$$\ln(A^2T)' = 0.172813 \ln^2 PV + 0.210012 \ln PV + 3.581252 \equiv g'[\ln PV] \quad (16)$$

Therefore, $$\frac{I_1}{I_2} = e^{[g'(\ln PV_1) - g'(\ln PV_2)]} \quad (17)$$

When monitoring opacity, the camera may be set with the aperture fixed at a minimum value, e.g., F8, so that only the shutter speed needs to be adjusted to have the exposure fall into an acceptable dynamic range. Therefore, the radiance ratio between any two small areas of the photo is quantified from the respective pixel values using the method described above. The resulting opacity value is then determined with a contrast or transmission model as described below.

Calibrating a camera without a manual mode setting. Most inexpensive digital cameras do not have a manual mode to control exposure time and aperture size as is needed to calibrate the camera as described above. For these automatic cameras, a response curve may be calibrated by employing a manual mode digital camera or a luminance meter together with the automatic camera.

Figure 3:
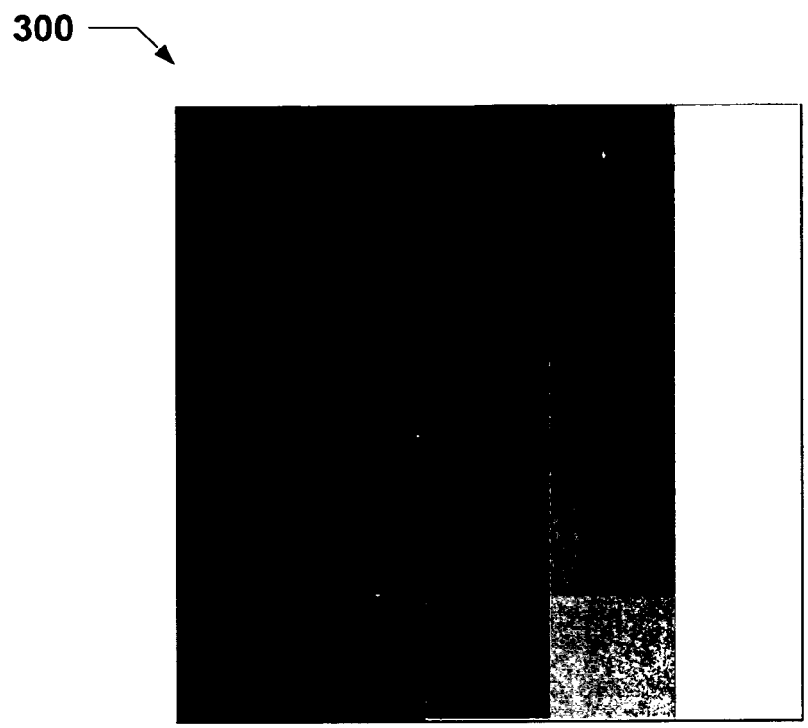
FIG. 3 depicts a grid that may be used to calibrate an automatic digital camera by using a light meter or a digital camera having manual exposure control.

Photographs of a grid as depicted in FIG. 3 are taken from the same location with both the automatic camera and the manually controlled camera to provide a range of luminance values. The response curve of the manual camera is used to determine the relative luminance of each sector in the grid. The average pixel value of each sector is also available from the automatic camera. The response curve of the automatic camera is then generated from a least squares regression between the pixel values of the grid sectors taken with the automatic camera and the corresponding relative luminance values from the manual camera or luminance meter. Radiance ratios are then determined as described above for the manual mode camera. Calibration of a camera is best performed during the generation of stable radiance values from a light source and the detection of those values by the camera. Such condition may be best attained during indoor testing so that temporal change in radiance values by the sun does not influence the calibration of the camera.

Quantification of Opacity using Contrast and Transmission Models. Based on the DOM™ employing a "calibrated" digital camera as described above, either a contrast model or a transmission model, or both, may be used to determine opacity of a subject, such as plumes from smoke stacks. Each model has unique advantages and limitations that depend at least partially on environmental conditions at the site of the plume.

Contrast Model. The contrast model determines opacity based on the contrast between two backgrounds. One background is located behind the "subject," e.g., a plume, while the other background is located near the first background, but is not blocked by the subject. The background located behind the subject may be termed the "target," and the background located beside the subject may be termed the "reference." The contrast model allows for the quantification of opacity, e.g., for white, black or gray plumes, independent of the background, e.g., the sky. Thus, a clear sky or homogenous white background conditions, e.g., a blue sky or an overcast cloudy sky, are not needed to implement a contrast model.

The target and reference backgrounds of the contrast model need surfaces with inherent contrast, e.g., a surface with white and black areas, so that the difference in contrast between the target and reference backgrounds can be assigned to that of the opacity of the subject. Additionally, the "compared" portions of the target and reference backgrounds should have the same reflectivity. For example, the black part of the target background should have the same surface reflectivity as the black part of the reference background. Moreover, the dark and light surfaces, e.g., black and white flat-painted surfaces, of each artificial background should be uniform and permit diffusive reflection.

Figure 4:
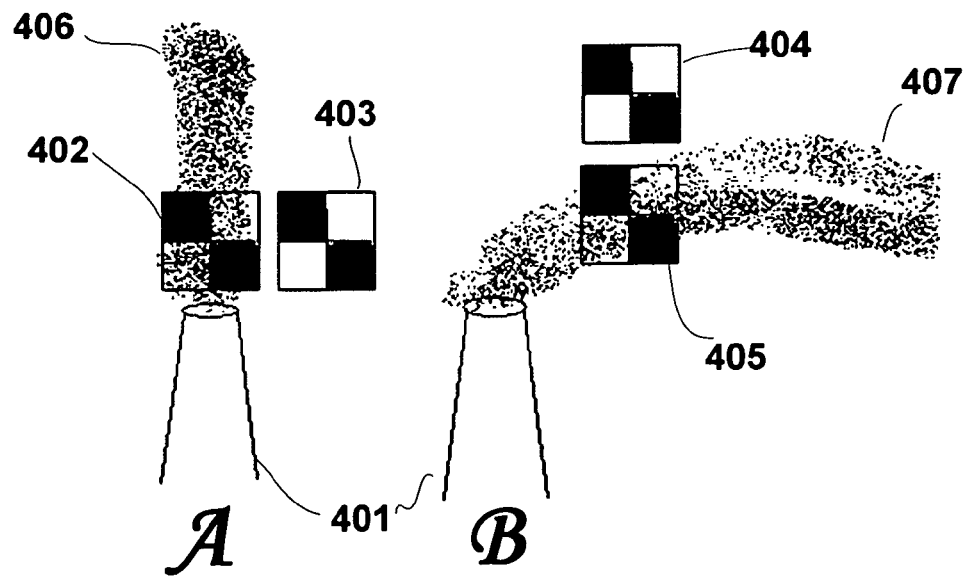
FIG. 4A depicts a first configuration for use with a contrast model that may be employed with select embodiments of the present invention.
FIG. 4B depicts a second configuration for use with a contrast model that may be employed with select embodiments of the present invention.

For select embodiments of the present invention, the position of backgrounds behind smoke stacks 401 may be as depicted in FIG. 4. The reference background 403 may be located to the right or left side of the vertical plume 406 "obscuring" the target background 402. For horizontal plumes 407, the reference background 404 may be located above or below the plume 407 but the target background 405 must be placed to account for wind direction. For horizontal sources at ground level, the target background 405 may be located near the ground and the reference background 404 may be located either upwind or above the plume 407 so that the plume 407 does not influence the transmission of light between the camera 703 (FIG. 7) and reference background 404.

Figure 5:
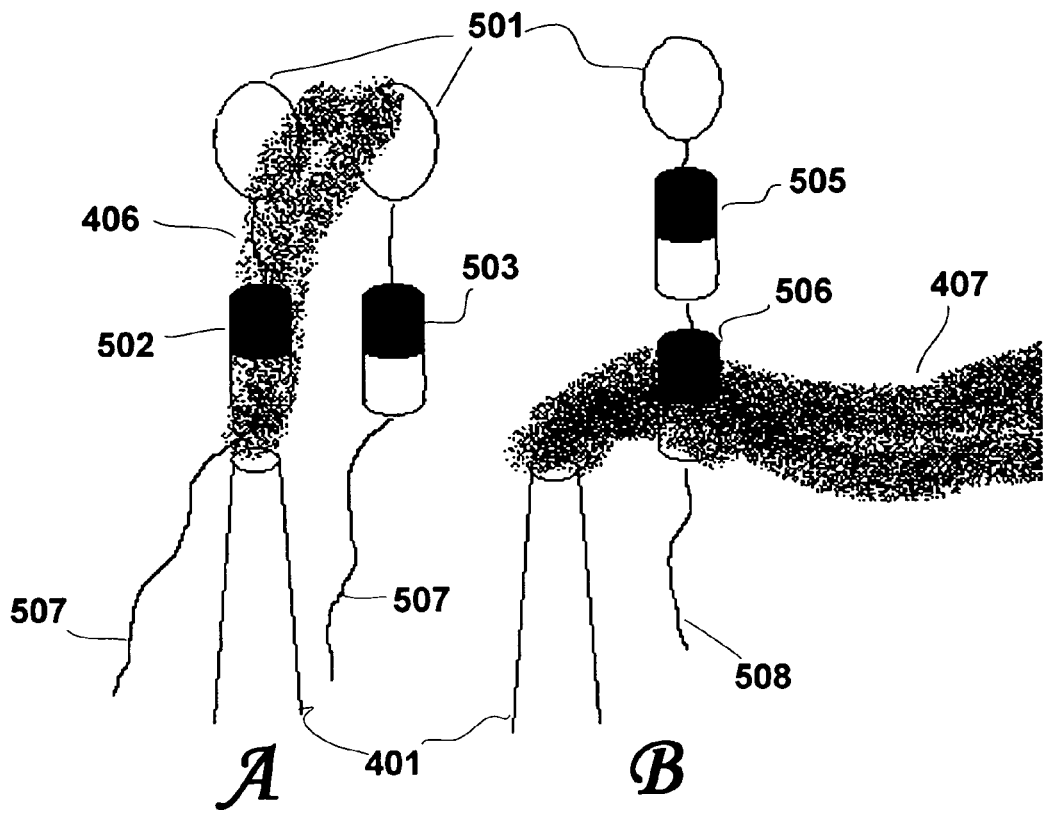
FIG. 5A depicts a third configuration for use with a contrast model that may be employed with select embodiments of the present invention.
FIG. 5B depicts a fourth configuration for use with a contrast model that may be employed with select embodiments of the present invention.
Figure 6:
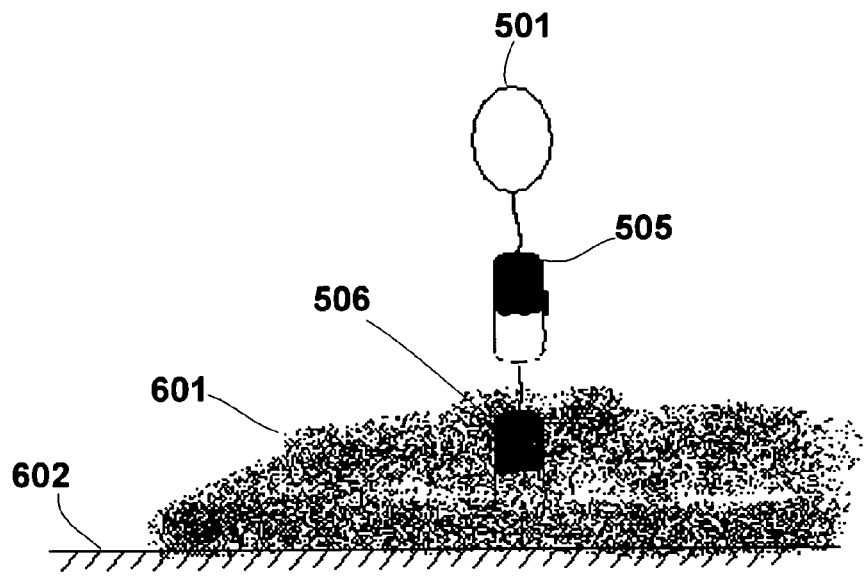
FIG. 6 depicts a fifth configuration for use with a contrast model that may be employed with select embodiments of the present invention.

Artificial backgrounds may be as simple as a board that is painted black and white (as shown in FIG. 4 at 402-405) and attached to the stack 401 for routine monitoring of opacity. Of course, artificial backgrounds must be kept clean to afford a proper reference. This may present a problem when environmental conditions impact the finish of the artificial backgrounds, e.g., the plume impinges either the reference or target artificial backgrounds, or both, at certain times and contributes to discoloration. Appropriate backgrounds may also be as simple as the surface of a building behind the plume as long as the surface is uniform and permits suitable diffusive reflection, e.g. painted with flat paint and maintains consistency from one measurement period to the next. In select embodiments of the present invention, another simple and effective means to provide target and reference backgrounds for an elevated point source 406, 407 or a ground level area source 601 is to use two objects, e.g., cylinders 502, 503, 505, 506, hanging under one or two balloons 501 as depicted in FIGS. 5 and 6, respectively. The balloons 501 may be tethered with a suitable rope 507, 508 or released to fly away vertically and horizontally while taking digital photos thereof.

Figure 13:
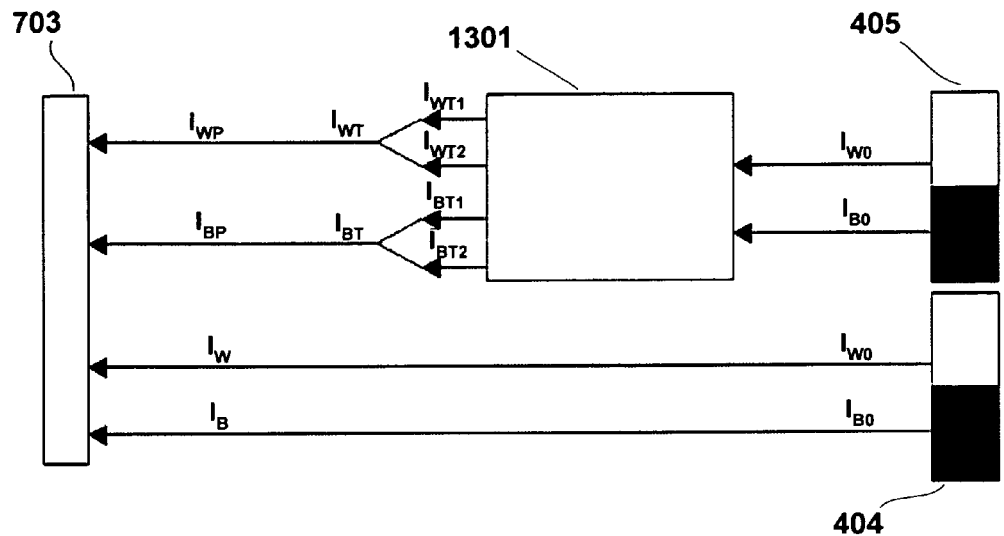
FIG. 13 depicts the relationships between radiance values presented to a camera from a reference background placed to the side of a subject of interest and a target background placed behind a subject of interest as may be used with a contrast model in embodiments of the present invention.

Refer to FIG. 13. The contrast model relies on the difference between the contrast of the bright/dark surface for each of the two contrasting backgrounds, the target 405 background that is behind the subject 1301, e.g. a smoke plume, and a reference 404 background that is located beside or just above the subject 1301. $I_{W0}$ and $I_{B0}$ are radiance values for ambient light from the white portion and black portion, respectively, of the artificial backgrounds 404, 405. $I_{WT1}$ and $I_{BT1}$ are the attenuated radiance values that result from $I_{W0}$ and $I_{B0}$, respectively, after $I_{W0}$ and $I_{B0}$ pass through the subject 1301, e.g., a smoke plume. $I_{WT2}$ and $I_{BT2}$ are radiance values caused by diffusive scattering from the portions of the subject (plume) 1301 in front of the white and black sections, respectively, of the target background 405. These diffuse radiance terms are caused by sources of light radiance other than directly from the artificial target background 405, e.g., sunlight back-scattered from the subject 1301 and directed into the line of sight of the camera 703 toward the subject 1301. $I_{WT}$ is the radiance value resulting from summing $I_{WT1}$ and $I_{WT2}$, and $I_{BT}$ is the radiance value resulting from summing $I_{BT1}$ and $I_{BT2}$. Finally, $I_{WP}$ and $I_{BP}$ are the equivalent radiance values recorded by the camera 703, in terms of pixel values (PVs), that are related to $I_{WT}$ and $I_{BT}$, respectively, assuming atmospheric optical depth is nil between the camera 703 and the subject 1301. Optical depth is the product of the extinction coefficient of the atmosphere in the path and the path length, e.g., distance between the camera 703 and the reference target 404. Similarly, $I_W$ and $I_B$ are the equivalent radiance values recorded by the camera 703, in terms of pixel values, that are related to $I_{W0}$ and $I_{B0}$, respectively, which originated from the reference background 404 that is not obscured by the subject 1301. Again, $I_W$ and $I_B$ are assumed to be unaffected by optical depth between the camera 703 and the reference background 404, so that $I_W=I_{W0}$ and $I_B=I_{B0}$ as discussed below. Thus, only values for $I_{WP}$, $I_{BP}$, $I_W$, and $I_B$ are needed to determine opacity, $O_C$, as determined by the contrast model and described by:

$$O_C = 1 - \frac{I_{WP} - I_{BP}}{I_W - I_B} \qquad (18)$$

Eqn. (18) is valid if the optical depth of the unobstructed path between the target 1301 and reference background 404 and the camera 703 is much less than the optical depth of the subject 1301, e.g., a smoke plume. As an example, for field tests conducted at Springfield, Ill., the optical depth of the plume was characterized with an opacity value of 5%. The optical depth of the unobstructed atmosphere at Springfield is based on a mean total light scattering coefficient for aerosol particles (as measured at the Bondville Environmental Aerosol Research Site located 134 Km from Springfield) of 26.9±28.3 Mm$^{-1}$ (Carrico, C. M. and M. J. Rood, *Journal of Geophysical Research*, 103, 565-574, 1998), an average single scattering albedo of 0.91 (Delene, D. J. and J. A. Ogren, *Journal of Atmospheric Sciences*, 59, 1135-1150, 2002), a Rayleigh scattering coefficient of the atmosphere of 13.2 Mm$^{-1}$ at sea level (Sloane, C. S. et al., *Aerosol Science and Technology*, 14, 289-301, 1991), negligible absorption of visible light by gases, and a path length of 30 m between the camera 703 and the artificial target 405 and reference 404 backgrounds. The resulting optical depths for the plume 1301 and for the unobstructed atmosphere are 5.13×10$^{-2}$ and 0.13× 10$^{-2}$, respectively. Thus, the optical depth of the plume is 38.5 times larger than the optical depth of the unobstructed atmosphere. The Beer-Lambert Law (Opacity=$1-e^{-optical\ depth}$) indicates that the unobstructed atmosphere contributes 2.5% and the plume contributes 97.5% of the total opacity for the unobstructed atmosphere and plume for the conditions cited above, resulting in a negligible contribution to opacity by the unobstructed atmosphere.

The position of the sun relative to the camera 703 affects the values of $I_{WT2}$, in turn influencing the overall contrast between the subject 1301 and its background 404, 405. According to Lorenz-Mie theory, there is more light scattered in the forward direction with increasing particle diameter. Liou, K. N., Ed., *An Introduction to Atmospheric Radiation*; Academic Press, San Diego, Vol. 84, 2002. Hence, the radiance from the subject (plume) 1301 is larger if the sun is located in front of the camera 703 as compared to behind the camera 703. Therefore, for the field test at Springfield, the sun was oriented to the back of the camera 703 to minimize $I_{WT2}$. It is most likely for this reason that USEPA Method 9 requires the sun to be within a 140° sector to the back of the observer.

In summary, a contrast model objectively quantifies opacity regardless of ambient conditions. With reference to the camera lens, the contrast model establishes a ratio of the radiance of objects, i.e., artificial backgrounds, behind and next to the source, e.g., a smoke stack. The masking of visible light by the subject, e.g., a smoke plume, results in a computed radiance ratio other than 1:1 that is directly related to opacity as given in Eqn. (18).

Transmission Model. In select embodiments of the present invention, the transmission model determines opacity based on the contrast between the subject and its natural background, e.g., a smoke plume and the sky, a smoke plume and a building, and the like. In select embodiments of the present invention, this method is recommended for quantifying the opacity of dark or light plumes having a uniform contrasting background, e.g., clear blue sky for white or black plumes, or a bright overcast sky or light colored building for dark plumes, and the like.

A transmission model quantifies opacity of the subject, e.g., a smoke plume, by comparison with an existing contrasting uniform background. For example, a clear sky would be a suitable background for either white or black smoke plumes, and a uniform overcast sky would be suitable for black smoke plumes. Recall that the contrast model is based on the change in contrast for one image behind and one image near the plume, requiring four sectors to be chosen from a digital photo. The transmission model is based on the reduction of radiance from the plume and its background, requiring two sectors to be chosen from the digital photo. Thus, a transmission model may determine opacity based on the contrast between the subject and a "uniform" ambient background, such as the sky, a mountain, a building, and the like, or an artificial background such as a painted panel.

Figure 14:
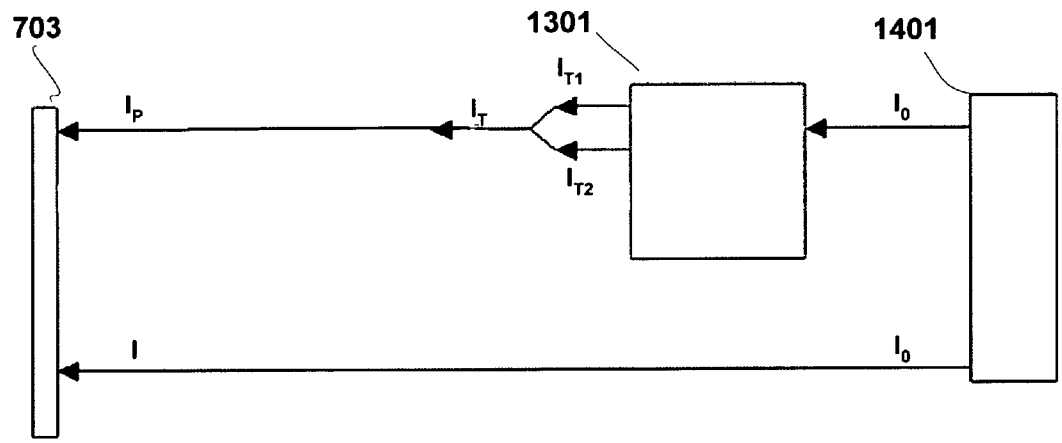
FIG. 14 depicts the relationships between radiance values presented to a camera from a natural background, such as sky, at the side of a subject of interest and a natural background, such as sky, behind a subject of interest as may be used with a transmission model in embodiments of the present invention.

Refer to FIG. 14. The transmission model quantifies opacity based on comparing the radiance from the subject 1301 with the radiance from the single uniform background 1401. $I_0$ is the radiance value from a uniform background 1401 that is located both behind and next to the subject 1301 (typically a smoke plume) and at the same height, e.g., uniform clear or overcast sky as background to a tall smoke stack. $I_{T1}$ is the attenuated radiance value that results from $I_0$ after the subject 1301 attenuates ambient light from the background 1401, and $I_{T2}$ is the diffusive radiance value caused by sources of light other than from the uniform background 1401, e.g., the sky light scattered by a smoke plume and directed into the line of sight of the camera 703. $I_T$ is the radiance value resulting from $I_{T1}$ and $I_{T2}$. Finally $I_P$ and I are the equivalent radiance values (in PVs) recorded by the camera 703. Thus, $I_P=I_T=I_{T1}+I_{T2}$ and $I=I_0$, since atmospheric contributions are assumed nil as discussed previously. Therefore, only the values for $I_P$, $I_{T2}$ and I are needed to determine opacity, $O_T$, as determined by the transmission model and described by:

$$O_T = 1 - \frac{I_P - I_{T2}}{I} \quad (19)$$

where $I_{T2}$ can be characterized based on the aerosol optical properties and the radiance from the sky background. See Kim et al. (2006).

Each model has its unique advantages and disadvantages. For example, a contrast model does not require a clear sky background and is able to determine opacity over a wide range of plume colors. It does, however, require backgrounds with inherent contrast both behind and next to the subject. Further, the determination of plume opacity is limited to those areas where the appropriate backgrounds are located. The transmission model does not require artificial backgrounds with inherent contrast both behind and next to the subject and, given a suitable uniform contrasting background, e.g., clear sky with respect to a plume, is able to determine opacity at any part of the subject, e.g., a smoke plume. However, the transmission model requires uniform backgrounds, e.g., clear sky, overcast sky, mountains, buildings and the like.

The contrast model and transmission model were further developed for DOM™ to quantify plume opacity during low ambient light and night conditions. The contrast model requires that a contrasting artificial background is placed both behind and beside the plume and sufficient light is available to illuminate the background for a digital camera to photograph both the plume and the artificial background. The transmission model requires only a dark sky as a background with the plume illuminated to permit photographing the plume and its dark-sky background.

Figure 18:
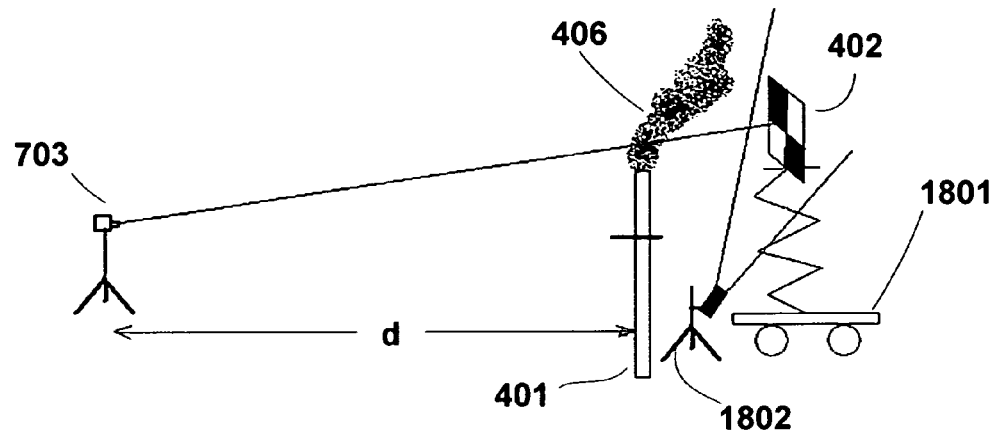
FIG. 18 is an elevation view of a night test configuration for the contrast model used in testing select embodiments of the present invention.

Quantification of plume opacity at night or in bad lighting using the contrast model. Refer to FIG. 18. Artificial backgrounds 402 with contrasting surfaces, e.g., black and white sections, are placed behind and beside a plume 406. A light source 1802 directly illuminates the artificial backgrounds 402 from behind the plume 406, and the plume 406 is photographed against the backgrounds 402.

The plume 406 can scatter, absorb, or both scatter and absorb, the incident light from its background resulting in light extinction. Refer again to FIG. 13 illustrating the transmission of light from the backgrounds 404, 405 (artificially illuminated in bad light or at night) towards the camera 703 as the light passes through ($I_{WP}$, $I_{BP}$) and beside ($I_W$, $I_B$) the targeted subject 1301, typically a smoke plume.

Refer again to Fig. 13. $I_{WO}$ and $I_{BO}$ are radiances emitted directly from the white and black areas, respectively, of the artificial background 404 beside the target 1301. $I_W$ and $I_B$ are radiances from the white and black areas respectively of the artificial reference background 404 beside the target background 405 as received by the CCD of the digital camera 703 without any attenuation of light caused by the target 1301. $I_{WT1}$ and $I_{BT1}$ are light radiances from $I_{WO}$ and $I_{BO}$ at the target background 405, but attenuated by the target 1301 due to scattering, absorption, or both scattering and absorption of light by the target 1301. $I_{WT2}$ and $I_{BT2}$ are the light radiances from directions other than from the artificial target background 405 that are scattered along the sight path of the camera 703. $I_{WT}$ is the resulting radiance from $I_{WT1}$ and $I_{WT2}$. $I_{BT}$ is the resulting radiance from $I_{BT1}$ and $I_{BT2}$. $I_{WP}$ and $I_{BP}$ are the radiances that are detected by the camera 703 caused by $I_{WT}$ and $I_{BT}$ respectively plus the influence of path extinction between the target 1301 and camera 703. If the path extinction is ignored, which is small when the target 1301 is within 1 Km of the camera 703, the radiance received by the camera 703 can be expressed as:

$$I_{WP}=I_{WT}=I_{WT1}+I_{WT2}=I_{W0}(1-O)+I_{WT2}=I_W(I-O)+I_{WT2} \quad (21)$$

$$I_{BP}=I_{BT}=I_{BT1}+I_{BT2}=I_{B0}(1-O)+I_{BT2}=I_B(1-O)+I_{BT2} \quad (22)$$

where O is opacity defined as 1 minus attenuated light radiance divided by initial light radiance. $I_{WT2}$ and $I_{BT2}$ can be neglected during nighttime conditions, since the light radiance from other directions is typically very low compared with the light coming from the illuminated artificial background 404, 405. From Eqns. (21) and (22):

$$I_{WP}-I_{BP}=(I_W-I_B)(1-O) \quad (23)$$

Therefore, $$O = 1 - \frac{I_{WP} - I_{BP}}{I_W - I_B} \quad (24)$$

Figure 19:
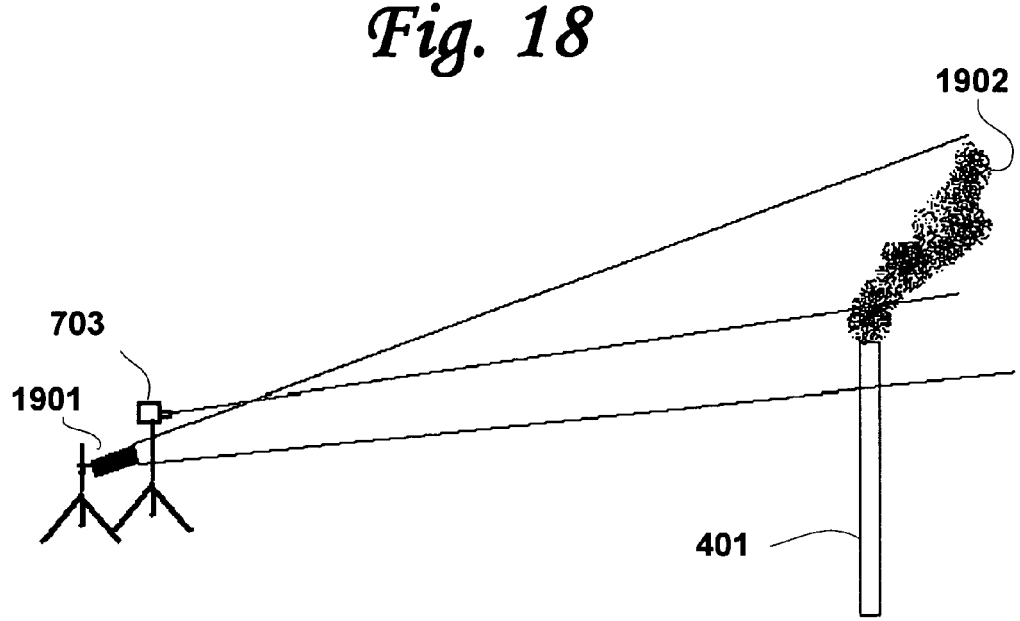
FIG. 19 is an elevation view of a night test configuration for the transmission model used in testing select embodiments of the present invention.

Quantification of opacity using the transmission model. Refer to FIG. 19. In this model, no artificial backgrounds 404, 405 are required. A light source 1901 shines light directly into the target 1902, typically a plume 406. The camera 703 photographs the illuminated target 1902 against the dark sky.

Under these conditions, the target 1902 will backscatter incident light to the camera 703. Ambient light is typically negligible compared with the light source 1901 during nighttime. Also, the path extinction and radiance are ignored when the camera 703 is within 1 Km of the target 1902.

Figure 20:
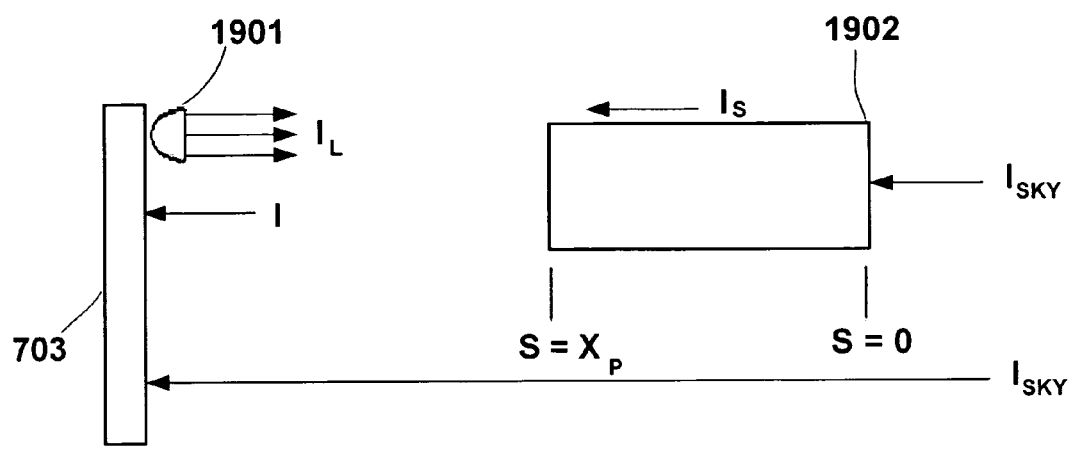
FIG. 20 depicts the relationships between radiance values presented to a camera from an ambient night sky reference background at the side of a subject of interest and an ambient night sky target background behind a subject of interest as may be used with a transmission model in embodiments of the present invention.

Refer to FIG. 20 illustrating the light transmission mechanism further described below. $X_P$ is the depth of the target 1902. The transfer of light toward the camera 703 is described by:

$$\frac{dI_s}{ds} = -s_s I_s - s_a I_s + \sigma_a B(T) + \quad (25)$$

$$\frac{s_s}{4p}\int_0^{2p}\int_{-1}^{1} I_{sky} P(q) dm df + I_L \frac{P(\theta)}{4\pi}\omega\sigma_e + S_0 e^{-t/m_0}\frac{P(q)}{4p} w s_e$$

Where:
$I_L$=radiance from the light source;
$I$=radiance received by the camera;
$I_S=I_s(\lambda, s, \mu, \phi)$, radiance at coordinate S;
$\lambda$=wavelength of light;
$S$=location;
$\mu$=cos(zenith angle);
$\phi$=azimuth angle;
$I_{SKY}$=radiance from the sky background;
$\sigma_s=\sigma_e\cdot\omega$, scattering coefficient;
$\sigma_a=\sigma_e\cdot(1-\omega)$, absorption coefficient;
$\sigma_e=\sigma_s+\sigma_a$, extinction coefficient;
$\omega$=single scattering albedo;
$B=B(T)$, thermal emission factor;
$T$=temperature;
$P=P(\theta)$, phase function;
$\theta$=scattering angle;
$S_0$=solar constant;
$\tau$=optical depth of the atmosphere; and
$\mu_0$=cos(solar zenith angle)

Radiation of visible light wavelengths is of interest, hence the thermal term ($\sigma_a B(T)$) can be neglected. Tests occur at night resulting in a negligible solar term $$\left(S_0 e^{-t/m_0}\frac{P(q)}{4p} w s_e\right).$$

Because ambient light is negligible compared to light from the light source 1901, contribution from the diffusive scattering term, $$\frac{s_s}{4p}\int_0^{2p}\int_{-1}^{1} I_{sky} P(q) dm df,$$

is also negligible. Therefore, Eqn. (25) becomes:

$$\frac{dI_s}{ds} = -s_e I_s + I_L \frac{P(q)}{4p} w s_e = -s_e(I_s - J) \quad (26)$$

where $$J = I_L \frac{P(q)}{4p} w \quad (27)$$

Separating the variables of Eqn. (26); integrating using the boundary conditions $I_S=I_{SKY}$ at S=0 and $I_S=I$ at $S=X_P$; and assuming the target 1902, typically a plume 406, is uniform along the path, yields:

$$\frac{I-J}{I_{sky}-J} = \exp(-s_e x_p) = 1 - O \quad (28)$$

and $$O = \frac{\frac{I}{I_{SKY}} - 1}{\frac{J}{I_{SKY}} - 1} \quad (29)$$

$$\frac{I}{I_{SKY}}$$

is determined from a photograph using the technique described above for calibrating digital cameras. Thus, only the parameter $$\frac{J}{I_{SKY}}$$

is needed to quantify opacity. However, the parameter, $$\frac{J}{I_{SKY}} = \frac{I_L}{I_{SKY}} \frac{P(\theta)}{4\pi} \omega,$$

is a function of the property, $I_L$, of the light source 1901, target type ($P(\theta)$, $\omega$) and ambient light condition ($I_{SKY}$). Thus, $$\frac{J}{I_{SKY}}$$

is calculated theoretically only when all the above conditions are known. However, this parameter can be determined practically from a photograph with known opacity under typical field settings. For example, with a photograph indicating 50% opacity, the radiance ratio between the target and sky, $$\frac{I_{P50\%}}{I_{SKY}}$$

can be determined by means of the camera response function obtained in initial calibration. Thus, the calibrated value for $$\frac{J}{I_{SKY}}$$

is:

$$\frac{J}{I_{SKY}} = \frac{1}{0.5}\left(\frac{I_{P50\%}}{I_{SKY}} - 1\right) + 1 \tag{30}$$

In summary, select embodiments of the DOM™ use the contrast model with artificial backgrounds or inherently contrasting backgrounds that already exist behind and near the subject, e.g., a plume, the transmission model, or both to objectively quantify the opacity of plumes under a much wider range of environmental conditions than existing systems. The field tests of the DOM™ at an EPA-certified smoke school in Springfield, Ill. yielded very encouraging results in terms of the EPA allowable average opacity deviation as described below.

Field Tests. Field tests occurred at a USEPA-approved smoke school in Springfield, Ill. with an EPA-certified smoke generator that was operated by Illinois EPA personnel. Springfield is a mid-latitude continental site located at 39° 48' N, 89° 39' W that is 182 m above sea level. The smoke generator produces black plumes by burning toluene, and white plumes by vaporizing and re-condensing diesel fuel. The opacity of the generated plume is modified by controlling the feed rates of the liquid toluene or diesel and air. A transmissometer in the stack measures the opacity directly.

Figure 15:
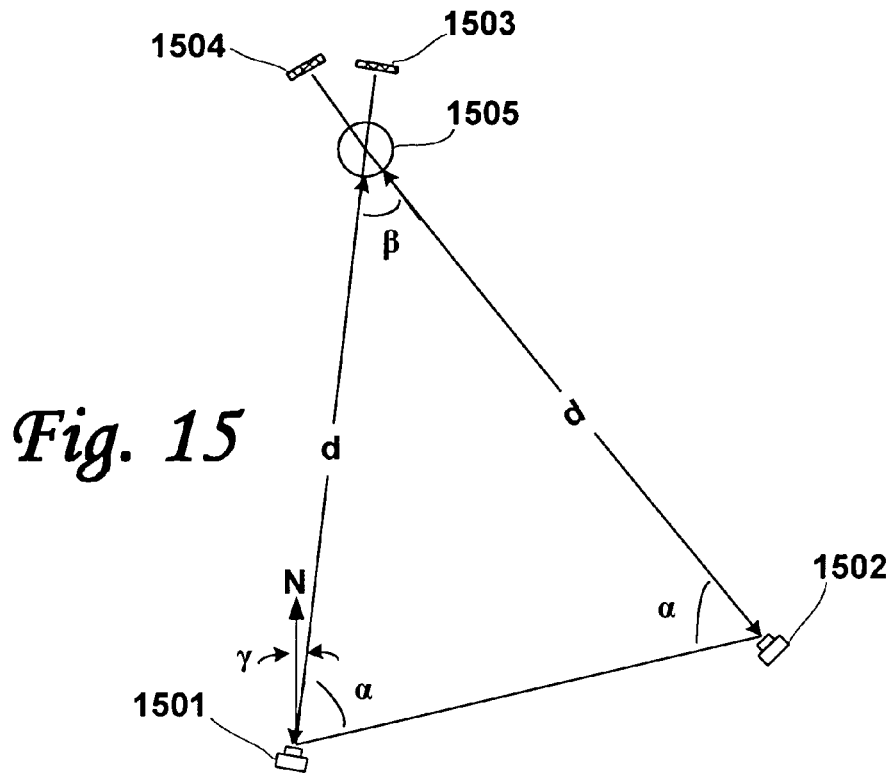
FIG. 15 is a plan view of a test configuration suitable for use with the contrast model as used in testing select embodiments of the present invention.
Figure 16:
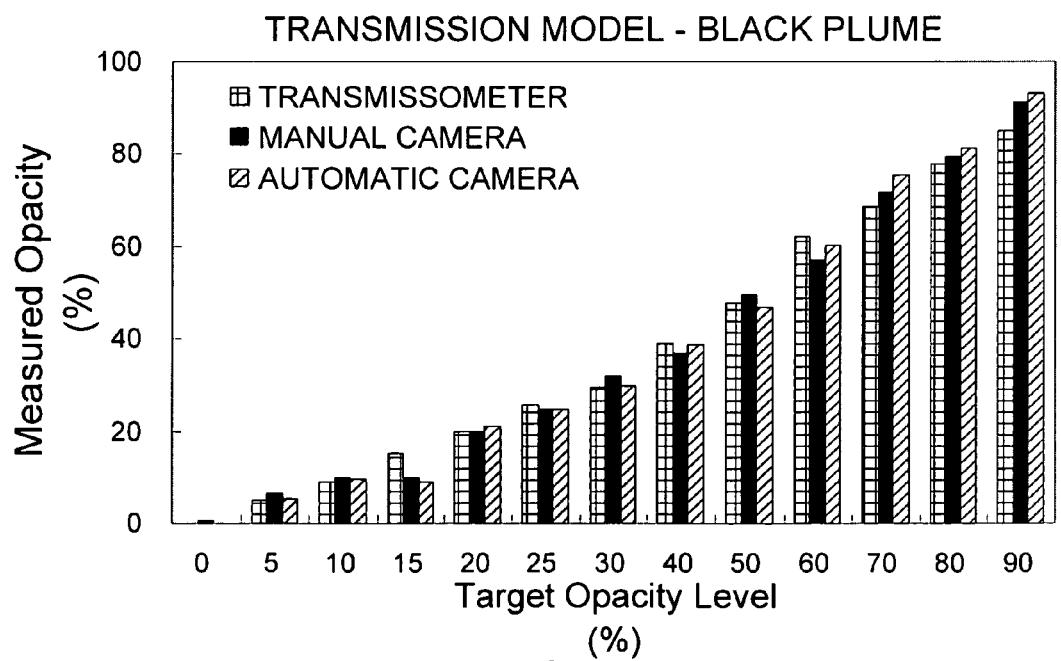
FIG. 16 is a graph of individual opacity versus target opacity level for black plumes as obtained using a transmission model with select embodiments of the present invention for both a manual and an automatic exposure camera.

Refer to FIG. 15 for a plan view of the test configuration of the first field test evaluating the performance of the DOM™ using both the contrast model with two identical artificial contrasting backgrounds 1503, 1504 (a reference and target background for each camera 1501, 1502 and the transmission model with a clear-sky background (background as depicted at 1401 in FIG. 14). For the contrast model, the reference background 1504 for the first camera 1501 is the target background 1504 for the second camera 1502 and the reference background 1503 for the second camera 1502 is the target background 1503 for the first camera 1501. The artificial backgrounds 1503, 1504 were oriented to point at a location between the cameras 1501, 1502 to make them point as much as possible to both cameras 1501, 1502. If there is no wind or wind blows in the same direction as a camera's line of sight, the target will be on the line of sight. When the wind blows different from the ideal condition, the target and reference can be changed. Two masts (not shown separately) were installed near the exhaust stack 1505 of the smoke generator (not shown separately) to mount the artificial contrasting backgrounds 1503, 1504 behind and beside the plume 406 (as depicted in FIG. 4A for a single camera's view of the configuration). The backgrounds 1503, 1504 are 90×90 cm square boards painted black and white in a checkerboard pattern. A first digital camera (CANON POWERSHOT® G3) 1501 capable of manual exposure control (hereafter "manual camera") was located to the west of the stack 1505 and an automatic-only digital camera (SONY® DSC-S30) 1502 (hereafter "automatic camera") was located to the east of the stack 1505. The first camera 1501 was oriented at an angle, γ, from North where γ is 15° to the East from north. The cameras 1501, 1502 were used simultaneously to quantify opacity (FIG. 15). The manual camera 1501 was set in the "aperture priority" mode at F8 to minimize vignetting effect and allow the most accurate calibration. Debevec, P. E. and J. Malik, *Recovering High Dynamic Range Radiance Maps from Photographs*, Computer Graphics Annual Conference Series, 369-378, 1997.

Each camera 1501, 1502 was positioned on a tripod (not shown separately) and located 1.4 to 1.7 m above the ground to provide a clear view of the plume 406 (as depicted in FIG. 4A) from the stack 1505. The position of the cameras 1501, 1502 and artificial backgrounds 1503, 1504 were arranged so that one artificial background 1503,1504 was behind the plume 406 and the other artificial background 1503, 1504 was next to the plume 406 for the orientation of each camera 1501, 1502. The stack 1505 is 30 cm in diameter and its outlet was 4.5 m above the ground. Both cameras 1501, 1502 were 21.4 m (d in FIG. 15) away from the stack 1505 to allow for a minimum distance of at least three stack heights between the cameras 1501, 1502 and the base of the stack 1505. This established an isosceles triangle with the equal sides, d, separated by a 45° angle, β, and the cameras 1501, 1502 being oriented to the smoke stack 1505 at a 67.5° angle, α, with respect to the baseline between the two cameras 1501, 1502.

A first test sequence started at 0% opacity and increased to 100% opacity at 14 levels for the black plumes. White plumes were generated with the same test sequence. Each camera 1501, 1502 took one photo every fifteen seconds for a total of twenty-four photographs/camera at each opacity level for each of the black and the white plumes. The test began at 9 AM CST and ended at 3 PM CST, resulting in 1,405 digital photographs. The sun was oriented within a 208° sector to the back of the cameras for the entire duration of the first test sequence. There were cloud-free conditions during the morning with the formation of overcast clouds during the afternoon. Hourly environmental conditions during the first test sequence are given in Table 1.

TABLE 1

Hourly weather conditions during the first test sequence.

| Time [hr:min] | Ambient Temperature [° C.] | Relative Humidity [%] | Pressure [hPa] | Wind Speed [km/hr] | Sun Position Altitude (degrees) | Sun Position Azimuth (degrees) |
|---|---|---|---|---|---|---|
| 8:54 | 20 | 78 | 1021 | 0.0 | 33 | 91 |
| 9:54 | 22 | 69 | 1021 | 5.6 | 45 | 102 |
| 10:54 | 23 | 57 | 1021 | 0.0 | 56 | 106 |
| 11:54 | 24 | 53 | 1021 | 7.4 | 65 | 137 |
| 12:54 | 26 | 54 | 1020 | 11.1 | 70 | 173 |
| 13:54 | 26 | 47 | 1020 | 9.3 | 67 | 211 |
| 14:54 | 26 | 47 | 1020 | 5.6 | 59 | 237 |

A second field test was completed with the same smoke generator used for the first test sequence. The test also occurred in Springfield during an EPA-approved smoke school, but at a different local site. The DOM™ was able to be evaluated in overcast conditions and intermittent rain. The sun was oriented within an 88° azimuth sector to the back of the camera for the duration of the second test sequence.

This second field site provided a roof (not shown separately) of a building as the dark background and a bright overcast sky (not shown separately) as the light background for the contrast and transmission models. The camera 1501 was located 30 m to the south of the smoke generator, i.e., d=30, and 1.4-1.7 m above the ground. The manual camera 1501 was set to the "aperture priority" mode at F8. The orientation of the camera allowed the background of the plume 406 (as in FIG. 4A) at 30 cm (one stack diameter) above the outlet of the stack 1505 to have contrasting backgrounds at the same height behind and next to the plume 406. This approach allowed for the use of the DOM™ contrast model to quantify plume opacity for both dark and light plumes 406 and the transmission model for dark plumes 406. The overcast sky precluded the use of the transmission model to determine opacity for light plumes 406 because of insufficient contrast. Therefore, the dark roof and the overcast sky backgrounds were used as the contrasting backgrounds for the contrast model during this second test sequence instead of the artificial reference 404 and target 405 backgrounds (black and white boards) used during the first test sequence. Thus, the change in contrast between the roof and sky backgrounds when observed through the plume and beside the plume 406 was determined from each digital photograph via employing the contrast model for both light and dark plumes 406 and for only the light plumes 406 using the transmission model as noted below.

The second test was done during a smoke school and consisted of two parts with the parts consisting of a first set of 25 randomly ordered black plumes 406 and a second set of 25 randomly ordered white plumes 406. This "smoke reading" portion of the smoke school was limited to a total of two parts during one day instead of the typical six to eight parts during two days. This was due to inclement weather that included cold temperatures, cloudy sky, high winds, and intermittent rain. See Table 2. Opacity values ranged between 5% and 80% for each set of the black and the white plumes 406. The camera 1501 took two photos for each opacity level (as established by the transmissometer), and the opacity values from those two digital images were arithmetically averaged to provide an individual DOM™—generated opacity. The tests occurred between 9 AM CST and 11 AM CST, and resulted in 100 photos.

All of the photos were analyzed for plume opacity using the contrast model. However, only the photos of black plumes 406 were analyzed using the transmission model because the overcast sky did not provide sufficient contrast between the white plumes and the overcast background. The target opacities ranged from 5% to 80% for both the black plumes and the white plumes during the two runs of the smoke school field test.

TABLE 2

Hourly weather conditions during the second test sequence.

| Time [hr:min] | Ambient Temperature [° C.] | Relative Humidity [%] | Pressure [hPa] | Wind Speed [km/hr] | Sun Position Altitude (degrees) | Sun Position Azimuth (degrees) |
|---|---|---|---|---|---|---|
| 8:54 | 10.6 | 71 | 1016 | 25.9 | 41 | 111 |
| 9:54 | 10.6 | 74 | 1015 | 24.1 | 52 | 127 |
| 10:54 | 11.1 | 69 | 1016 | 27.8 | 59 | 148 |

The opacity values obtained from the manual camera 1501 and the opacity values from the in-stack transmissometer are compared below.

Figure 17:
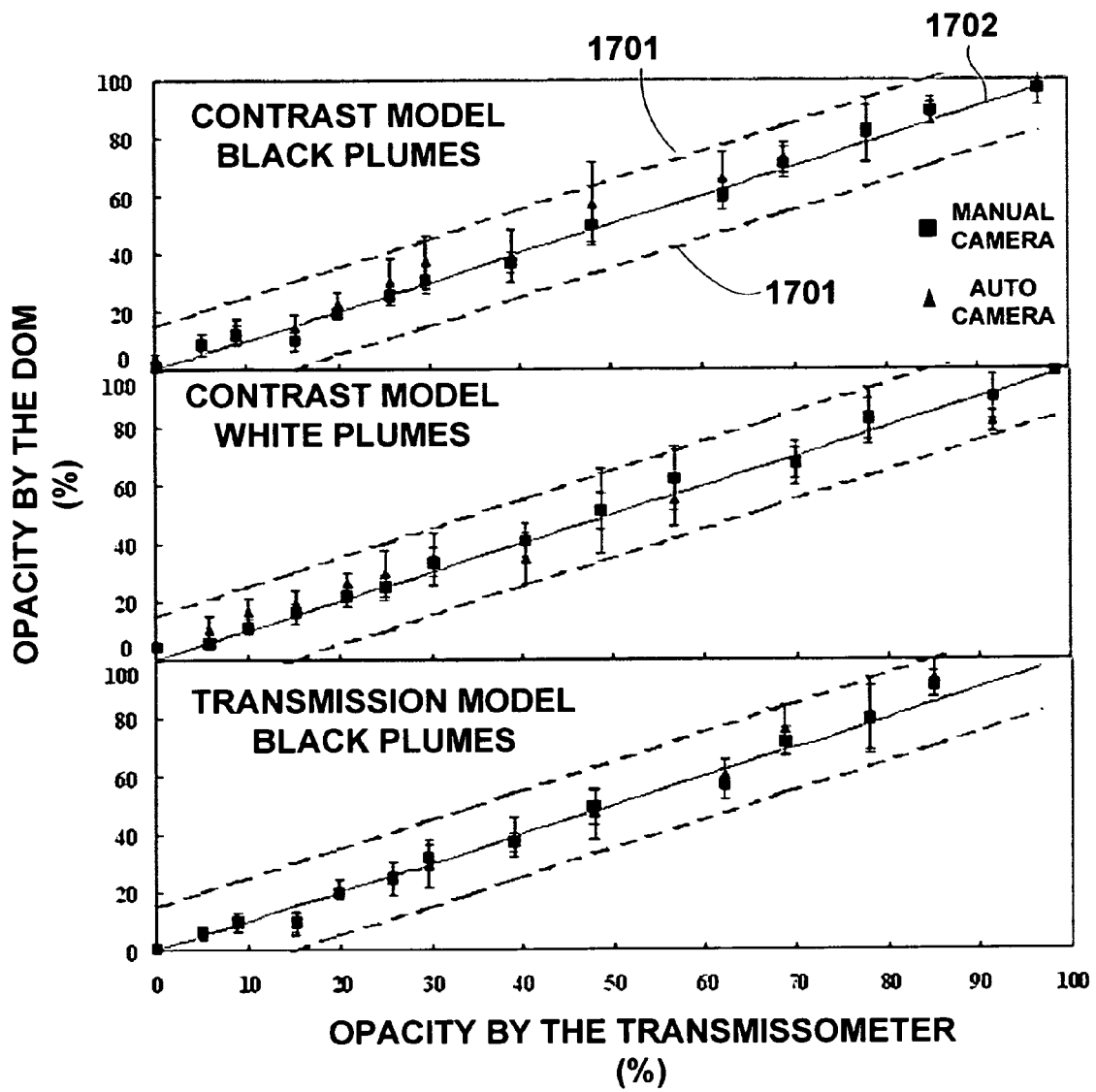
FIG. 17 is a graph of individual opacity values measured by select embodiments of the present invention compared to opacity measured by an in-stack transmissometer superimposed with error values from USEPA Method 9.

Refer to FIG. 17 in which individual opacity errors for results from the DOM™ are compared to the acceptable levels of error for both black plumes and white plumes. The solid line 1702 represents an ideal 1:1 correspondence between modeled opacity values obtained from the DOM™ and the measured opacity values that were obtained from the in-stack transmissometer. The dashed lines 1701 are USEPA's acceptable ±15% limit for an error in an individual measurement.

As shown in FIG. 17, results from the contrast model compare well to the results from the transmissometer with all of the individual errors less than 15%, and 95% of these results less than 7.5%. Results from the transmission model for black plumes also compare well to the results from the transmissometer with all of the individual errors being less than 15%, and 89% of these resulting in individual errors less than 7.5%. Therefore, the errors associated with the opacity values obtained with the contrast model and the transmission model (excluding white plumes with an overcast sky background) satisfy the individual error limits specified in USEPA Method 9. The results from both models exhibit linearity, i.e., $R^2$ values $\geq 0.97$ for all linear regressions.

All of the absolute average errors for both the contrast and transmission model results were <7.5%. Average errors using the contrast model were 2.2% for the manual camera 1501 and 4.3% for the automatic camera 1502. Average errors using the transmission model were 3.2% for the manual camera 1501 and 3.3% for the automatic camera 1502.

The DOM™ results for average errors with opacity ranges of 0%~40%, 0%~60% and 0%~100% were also compared with results from an ODECS test conducted under clear sky conditions at an USEPA-approved smoke school that was located in a high altitude desert environment. McFarland et al. (2003). The ranges of average opacity errors were chosen based on the availability of published ODECS data. McFarland et al. (2003). The comparison shows that the absolute average opacity errors from the DOM™ are 42-66% lower than the corresponding absolute average opacity errors from ODECS for black and white plumes and all opacity ranges. Du, K. et al., *Evaluation of Digital Image Method to Quantify Opacity of Stationary Source Plumes*, 97th Annual Meeting of the Air & Waste Management Association, 13, Indianapolis, Ind., 2004.

Figure 9:
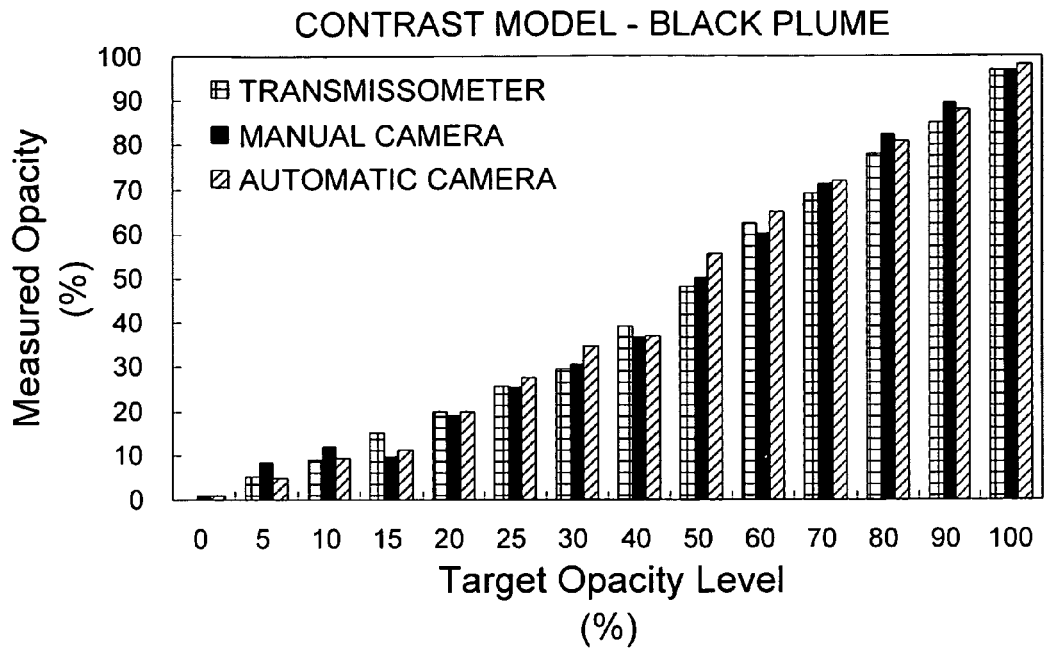
FIG. 9 is a graph of results comparing opacity values of black plumes as obtained with an in-stack transmissometer, and both an automatic exposure and a manual exposure (aperture priority) camera as obtained using a contrast model of an embodiment of the present invention.
Figure 10:
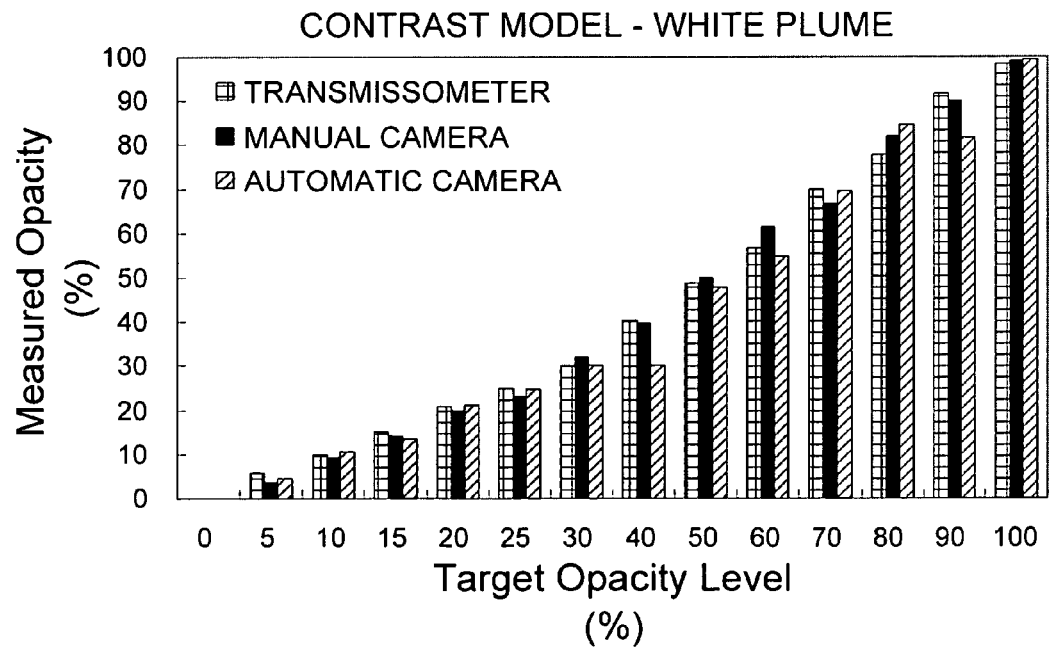
FIG. 10 is a graph of results comparing opacity values of white plumes as obtained with an in-stack transmissometer, and both an automatic exposure and a manual exposure (aperture priority) camera as obtained using a contrast model of an embodiment of the present invention.

Results using the contrast model while employing a manual camera 1501, an automatic camera 1502 and an in-stack transmissometer for the black plumes 406 are shown in FIG. 9. These results are for a field test in Springfield, IL. Results for the contrast model while using a manual camera 1501, an automatic camera 1502 and an in-stack transmissometer for the white plumes 406 are shown in FIG. 10. The target opacity was the preferred opacity value, which was similar to the value measured by the in-stack transmissometer once the smoke generator stabilized. The results from the models closely compare with the measured in-stack transmissometer results, but have more variation most likely because the transmissometer results are from the plume 406 confined in the stack 401. A confined plume is much more stable than an unconfined plume 406 subject to ambient conditions, such as wind and turbulence.

Figure 11:
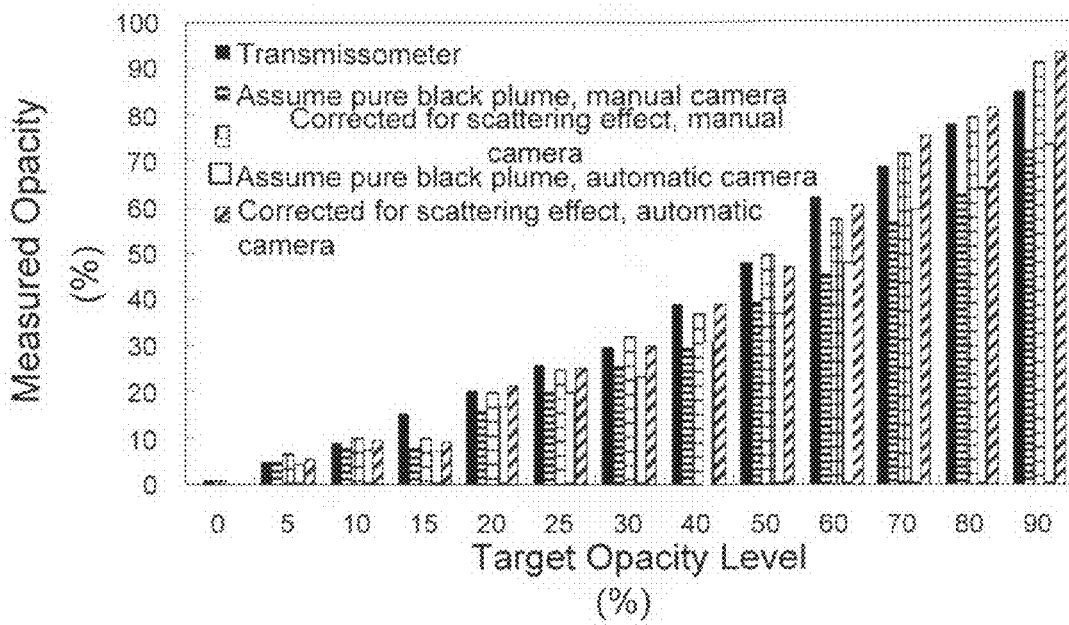
FIG. 11 is a graph of results comparing opacity values of black plumes as obtained with an in-stack transmissometer, and both an automatic exposure and a manual exposure (aperture priority) camera with assumptions as to background and corrections made to collected data, as obtained using a transmission model of an embodiment of the present invention.
Figure 12:
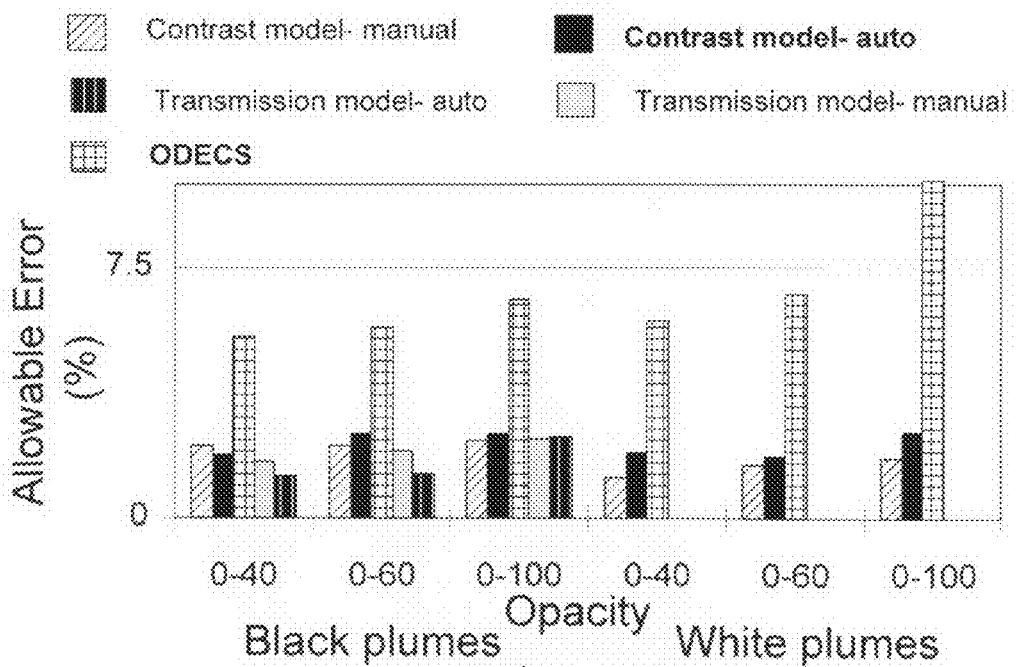
FIG. 12 is a graph comparing actual average absolute error to allowable error for black and white plumes for a manual and an automatic camera employing select embodiments of the present invention as well as for errors from the ODECS system.

Opacity results from the transmission model are provided in FIG. 11. Comparison of opacity measurements from both the contrast and the transmission models of the DOM™ and the ODECS method are presented in FIG. 12. The horizontal line defines the maximum allowable error established by USEPA Method 9. Absolute average deviations between transmissometer results and contrast model results are less than 3% for opacities in the measured ranges 0-40%, 0-60%, and 0-100% for both white and black plumes 406. The absolute average deviations are 60% below the maximum acceptable value of 7.5% as designated by USEPA Method 9, bettering the ODECS system in each category. Results obtained by employing the transmission model account for the scattering effect for realistic "black" plumes 406 that are not perfect light absorbers. In addition to applications for environmental monitoring, the DOM™ many be employed to determine scene contrast, e.g., the contrast between a mountain and its sky background, which may be used for quantitative estimation of visibility.

Average opacity error was in the range of 0.9-2.7% for the contrast model and 1.3-2.4% for the transmission model, well within the average error requirements of USEPA Method 9 (7.5%). The range of measured error for the contrast model was 0.1-10.4% and for the transmission model 0.1-6.6%, also well within the requirements of USEPA Method 9 for range of error.

USEPA Method 9 was developed to quantify plume opacity under daytime conditions. However, there are sources that have visible emissions during the night that also need to be characterized to readily monitor emissions at night. Therefore, a night field test was implemented at the Illinois EPA site to test the DOM™ ability to quantify plume opacity at night.

Figure 21:
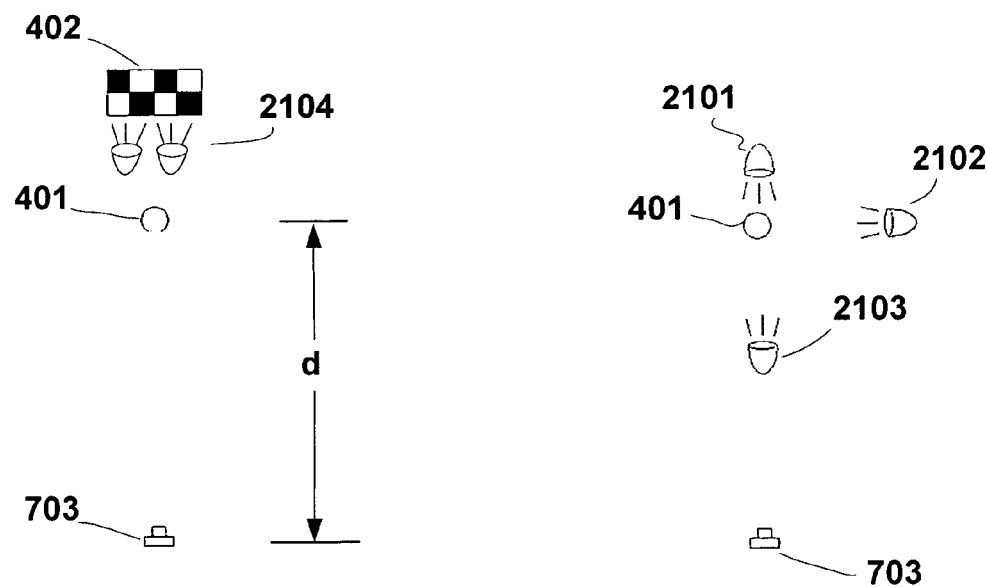
FIG. 21A is a plan view of an actual test configuration for the contrast model that was used in night testing of select embodiments of the present invention.
FIG. 21B is a plan view of three actual test configurations for the transmission model that was used in night testing of select embodiments of the present invention.

Field Test of DOM™ at night. Refer to FIG. 21A. A night field test was completed at Springfield, Ill. The contrast model was tested with two 500 W halogen light sources 2104 that were directed away from the plume 406 (not shown in FIG. 21A or B for clarity) and towards the contrasting artificial backgrounds 402 (only one shown in FIG. 21A for clarity), 403 (FIG. 4) that were located behind 402 and beside 403 the plume 406 (FIG. 4). Each of the artificial backgrounds 402, 403 consisted of eight black and white 45×45 cm squares painted on a board.

Refer to FIG. 21B. The transmission model was tested using one 500 W halogen light source that was placed at three locations: 2101, 2102, 2103. The light source has a concave reflecting lampshade to provide a collimated beam. Light from a first position ("Front light" 2103) was directed towards the plume from the stack 401 and away from the camera 703 along the same line as the camera 703 is oriented towards the stack 401. Light from a second position ("Back light" 2101) behind the stack 401 was directed towards the plume from the stack 401 in an orientation in line with and towards the camera 703. Light from a third position ("Side Light" 2102) was directed toward the plume from the stack 401 but at 90° from the line of orientation of the camera 703 to the stack 401. The camera 703 was positioned on a tripod (not shown separately) to provide a clear view of the plume 406 (FIG. 4) from the stack 401. The stack 401 is 4.5 m high and 30 cm in diameter. The horizontal distance, d, from the camera 703 to the stack 401 is set at 30 m so that it is greater than at least three times the stack height of 4.5 m. Cameras 703 used included a CANON POWERSHOT® G3 and two SONY CYBER-SHOT® Model P100, all operated in manual exposure mode.

Tests of black plumes started at 0% opacity, increasing to 100% opacity at ten levels. White plumes were tested with the same test sequence. Twelve photographs, one every 15 seconds, were taken at each opacity level for each of the black and white plumes. The night sky was clear during the tests. The weather conditions and sun positions for each hour during the test are summarized in Table 3.

TABLE 3

Hourly weather conditions during night testing

| Time | Ambient Temperature | Relative Humidity | Pressure | Wind Speed | Sun Position [degrees] | |
|---|---|---|---|---|---|---|
| [hr:min] | [° C.] | [%] | [hPa] | [Km/hr] | Altitude | Azimuth |
| Night 1 | | | | | | |
| 20:54 | 10 | 52 | 1021 | 14.8 | −25 | 308 |
| 21:54 | 9 | 50 | 1021 | 16.7 | −33 | 322 |
| 22:54 | 7 | 53 | 1022 | 16.1 | −39 | 339 |
| 23:54 | 7 | 51 | 1022 | 16.7 | −41 | 358 |
| Night 2 | | | | | | |
| 20:54 | 12 | 55 | 1023 | 9.3 | −25 | 309 |
| 21:54 | 12 | 55 | 1023 | 9.3 | −33 | 323 |
| 22:54 | 11 | 54 | 1024 | 16.7 | −38 | 340 |

Figure 22:
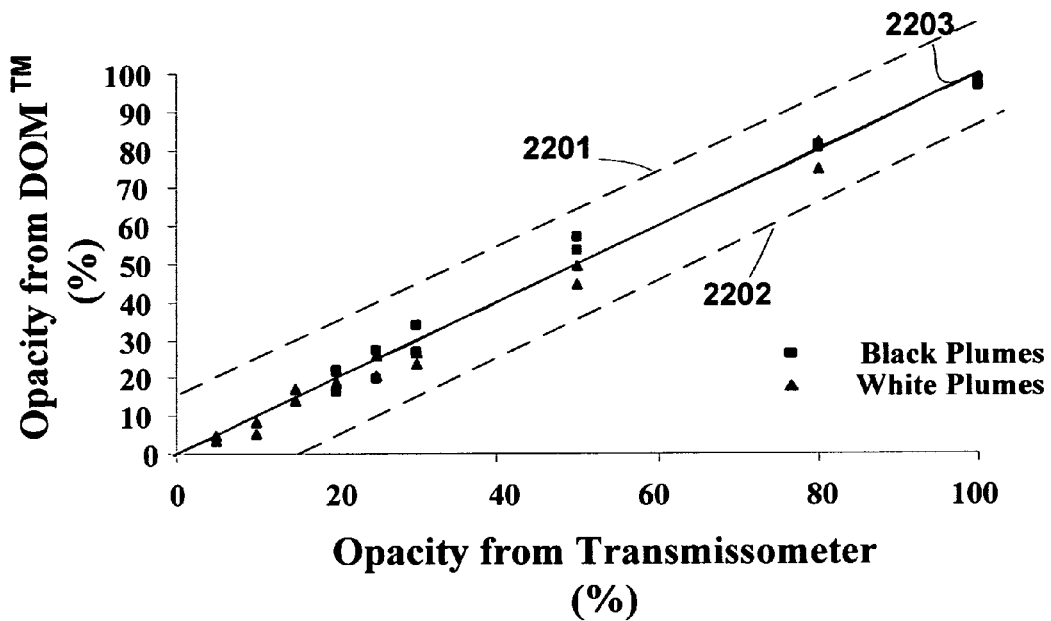
FIG. 22 is a graph of individual opacity values measured at night by a contrast model of select embodiments of the present invention compared to opacity measured by an in-stack transmissometer superimposed with lines describing 15% allowable individual error values as specified by USEPA Method 9.

Results from the contrast model. Refer to FIG. 22, a plot of individual opacity errors for results from the contrast model of the DOM™ as compared to the acceptable level of error established by USEPA Method 9. The solid line 2203 represents a perfect correspondence between opacity values from the models of the present invention as obtained from the DOM™ and the measured opacity values that were obtained from the in-stack transmissometer. The dashed lines 2001, 2002 represent the 15% error limit accepted by the USEPA for individual opacity measurements. Results from the contrast model compare well to the results from the in-stack transmissometer with all results well within USEPA standards, i.e., all individual errors ≦7.5% with average absolute opacity errors of 3.2% and 2.6% for the black and white plumes, respectively. Results also show linearity, i.e., $R^2$ values >0.98 for all linear regressions.

Figure 23:
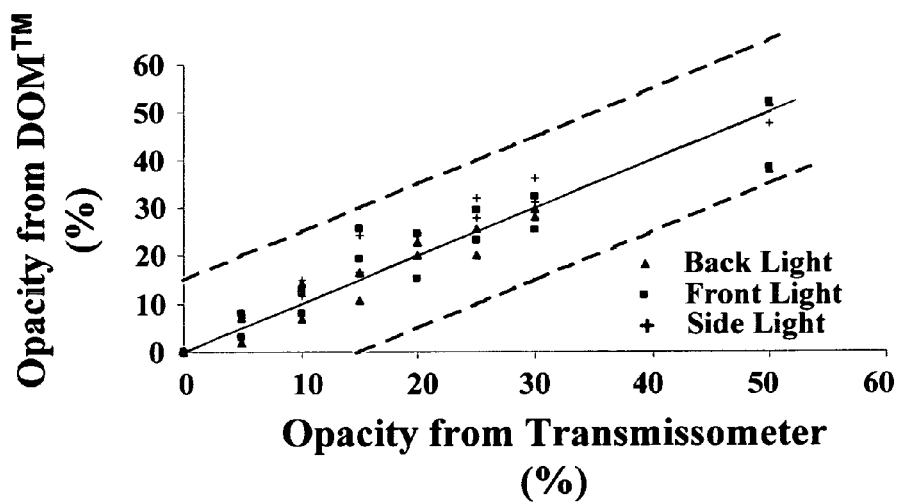
FIG. 23 is a graph of individual opacity values to 50% opacity measured at night by a transmission model of select embodiments of the present invention for each of three different lighting orientations as compared to opacity measured by an in-stack transmissometer superimposed with lines describing 15% allowable individual error values as specified by USEPA Method 9.

Results from the transmission model. Refer to FIG. 23 for individual night measurements of black and white plumes by the transmission model compared to that measured by the in-stack transmissometer. Results from the transmission model for opacity values from 0% to 50% compare well to the results from the transmissometer with all of the individual errors ≦15% and 92% of measurements ≦7.5%. For plumes 406 of opacity >50%, there was shadowing of the incident light by the plume 406 that caused non-uniform transmission of light through the plume 406, and the brightness of the plume 406 no longer increased monotonically with increasing opacity. Therefore, the transmission model was not used to quantify plumes of opacity >50%. Hence, errors obtained with the transmission model for opacity <50% satisfy the individual error limits set by the US EPA. Results from the transmission model are also linear, i.e., $R^2$ values >0.89 for all linear regressions.

Figure 24:
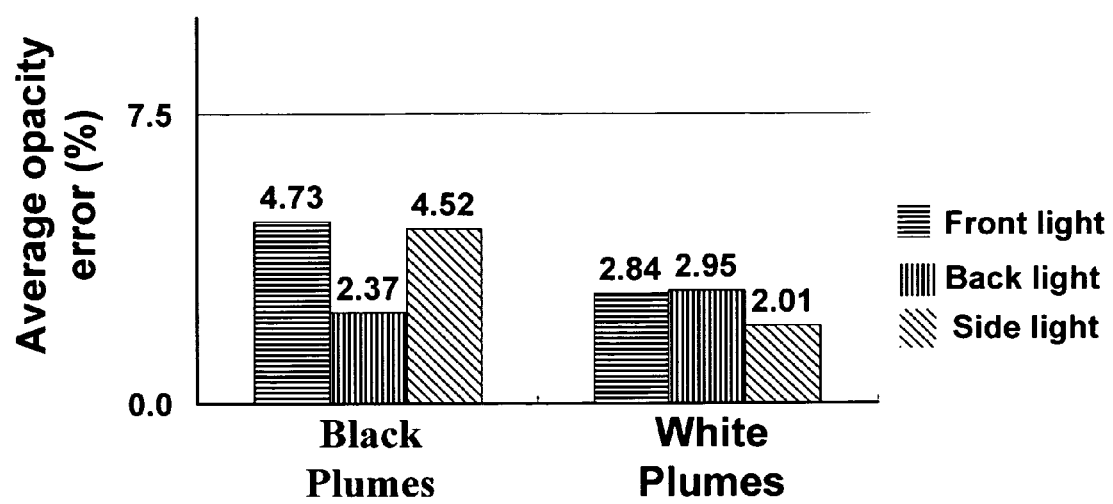
FIG. 24 compares averaged absolute opacity errors for night testing of both black and white smoke plumes using the transmission model of select embodiments of the present invention for each of three different lighting orientations.

Refer to FIG. 24. Average errors from tests employing the transmission model using the three light source locations 2101, 2102, 2103 were <7.5% for all plumes of opacity ≦50%. Average errors were 4.7% for black plumes and 2.8% for white plumes for front lighting 2103; 2.4% for black plumes and 2.9% for white plumes for back lighting 2101; and 4.5% for black plumes and 2% for white plumes for side lighting 2102. Lower average errors for both black and white plumes 406 when using back lighting 2101 most likely resulted from stronger scattering associated with forward scattering versus backscattering.

While the invention has been described in terms of some of its embodiments, those skilled in the art will recognize that the invention can be practiced with modifications within the spirit and scope of the appended claims. For example, although the system is described in specific examples for improving the determination of opacity of an airborne subject, such as a smoke plume, it may apply to any number of applications including non-airborne subjects, such as liquids including water and industrial solutions.

The abstract of the disclosure is provided to comply with the rules requiring an abstract that will allow a searcher to quickly ascertain the subject matter of the technical disclosure of any patent issued from this disclosure. 37 CFR § 1.72(b). Any advantages and benefits described may not apply to all embodiments of the invention.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Thus, it is intended that all matter contained in the foregoing description or shown in the accompanying drawings shall be interpreted as illustrative rather than limiting, and the invention should be defined only in accordance with the following claims and their equivalents.

We claim:

1. A method for obtaining an accurate quantitative measure of the opacity of a fluid, comprising:
   providing at least one image receiving device incorporating at least one light sensitive device;
   calibrating said image receiving devices,
   wherein said calibrating yields at least one response curve for each said image receiving devices, said response curve empirically based on a ratio of received radiances;
   employing at least one said image receiving device for taking images of said fluid, said images to include at least one background associated with said fluid;
   providing at least one algorithm based on a ratio of received radiances, said algorithm implemented in software on a computer readable medium;
   providing at least one processor for at least running said software;
   receiving and processing said image on at least one said processor; and
   analyzing said image using said algorithm and said software to obtain said measure of opacity,
   wherein said opacity may be measured under various ambient conditions, including measurement at night, and
   wherein said opacity may be measured under various ambient conditions without operator interpretation.

2. The method of claim 1 said fluid comprising at least one airborne fluid.

3. The method of claim 1 said fluid comprising at least one airborne effluent selected from the group consisting of: point source effluents, non-point source effluents, exhaust plumes, smoke, dust, and combinations thereof.

4. The method of claim 1 said fluid comprising at least one liquid.

5. The method of claim 1 said imaging receiving device comprising at least one camera.

6. The method of claim 1 said image receiving device comprising at least one digital camera,
   wherein at least one said digital camera incorporates manual exposure control.

7. The method of claim 1 said images comprising photographs.

8. The method of claim 1 said images comprising digital photographs taken in the visible light spectrum.

9. The method of claim 1 said background comprising backgrounds selected from the group consisting of: naturally occurring backgrounds, man made backgrounds, pre-specified man made backgrounds, and combinations thereof.

10. The method of claim 9 said algorithm comprising a contrast model establishing at least one ratio of the radiance of a first pre-specified background behind said fluid to the radiance of a second pre-specified background beside said fluid,
    wherein the relative positions of said first and second backgrounds are with respect to the orientation of the aperture of said image receiving device to said fluid, and
    wherein each of said first and second pre-specified backgrounds have contrasting at least one each light-colored and dark-colored portions.

11. The method of claim 10 said algorithm comprising:

$$O_C = 1 - \frac{I_{WP} - I_{BP}}{I_W - I_B}$$

where:
   $O_c$ is said accurate measure of the opacity of said fluid utilizing said contrast model,
   $I_{WP}$ is the radiance received at said image receiving device from said fluid obscuring at least one said light-colored portion of said first pre-specified background,
   $I_{BP}$ is the radiance received at said image receiving device from said fluid obscuring at least one said dark-colored portion of said first pre-specified background,
   $I_W$ is the radiance received at said image receiving device from at least one said light-colored portion of said second pre-specified background, and
   $I_B$ is the radiance received at said image receiving device from at least one said dark-colored portion of said second pre-specified background.

12. The method of claim 9 said algorithm comprising a transmission model establishing at least one ratio of the received radiance of a background having color contrast that is obstructed by said fluid to the received radiance of said background that is unobstructed by said fluid,
    wherein portions of said background are at least behind and beside said fluid with respect to the orientation of the aperture of said image receiving device, and wherein said background may be wholly natural, wholly man made, and combinations thereof, but is mostly uniform.

13. The method of claim 12 said algorithm comprising:

$$O_T = 1 - \frac{I_P - I_{T2}}{I}$$

where:
O$_T$ is said accurate measure of the opacity of said fluid utilizing said transmission model,
I$_{T2}$ is the diffusive radiance value caused by sources of light other than from said background,
I$_P$ is the radiance received at said image receiving device from said fluid obscuring a pre-specified uniform background behind said fluid and
I is the radiance received at said image receiving device from said background unobstructed by said fluid.

14. The method of claim 1 selecting said software from the group consisting of: Commercial-off-the-shelf (COTS) software, commercially available software, application specific software, custom software, shareware, freeware, and combinations thereof.

15. The method of claim 1 selecting said processors from the group consisting of: personal computers, computers, application specific integrated circuits (ASICs), personal digital assistants (PDAs), laptop computers, digital processors, and combinations thereof.

16. The method of claim 1 calibrating said image receiving device by obtaining a response curve for said image receiving device,
wherein said response curve describes the relationship between pixel values in said image obtained by said image receiving device and the exposure received by said light sensitive device, and
wherein said response curve provides a means to obtain from said pixel values the ratio of radiance values, I$_1$/I$_2$, of any two pixels of said image, where I$_1$ and I$_2$ are radiance values for said two pixels, respectively, and
wherein said response curve is used to obtain I$_1$/I$_2$ from said image.

17. The method of claim 16 further comprising empirically obtaining a response curve for at least one type of digital camera having a minimum resolution of approximately one megapixel and employing a charge coupled device (CCD) by:
fixing the aperture of said camera at a pre-specified value to minimize vignetting;
setting the sensitivity factor of said CCD at a pre-specified value,
wherein exposure is dependent upon only two variables, scene radiance, I, and exposure time, T;
selecting a homogeneous background suitable for diffusing at least energy in the visible light spectrum impinging thereon,
wherein an average of pixel values, PV$_{AVE}$, may be used to represent mean scene radiance, and
wherein homogeneous incident radiance is assumed over the area of the aperture of said camera;
taking photographs of said background,
wherein said photographs are taken during a pre-specified time interval, and wherein during each said interval said photographs are acquired using multiple different exposure times, and
wherein lighting conditions are stable to ensure constant scene radiance;
cropping each said photograph to employ the center of each;
determining PV$_{AVE}$ from said cropped photographs;
multiplying the square of the aperture diameter, A, by the exposure time, T, for each said cropped photograph;

$$\text{plotting } \ln(PV) \text{ versus } \ln\left(\frac{A^2 T}{A_{\min}^2 T_{\min}}\right),$$

wherein A$_{min}$ is the minimum aperture diameter setting and T$_{min}$ is the minimum exposure time used for said set of said photographs;
determining and plotting as a first curve a first set of data for ln(PV) vs. ln(A$^2$T)' from said digital images taken at a first level of radiance to yield incidence value, I$_1$;
determining and plotting as a second curve, approximately parallel to said first curve, a second set of data for ln(PV) vs. ln(A$^2$T)' from said digital images taken at a second level of radiance to yield incidence value, I$_2$,
wherein the relationships described by ln(PV) vs. ln(A$^2$T)' and obtained at different radiance values are parallel to each other, each point being obtained from one said digital photograph of said background, and
wherein said first and second curves are polynomial regression lines for said two sets of data, and
wherein a constant vertical distance between said two curves represents the constant ratio of the radiance values, ln(I$_1$/I$_2$).

18. The method of claim 17 in which said pre-specified value for aperture setting of said camera is F8 and said pre-specified value for sensitivity factor of said camera is ISO 100.

19. The method of claim 17 further comprising calibrating at least one digital camera having only automated exposure control by first calibrating a digital camera having manual exposure control and correlating photographs taken with said camera having manual exposure control to photographs taken with said camera having automated exposure control.

20. The method of claim 17 further comprising:
establishing the horizontal distance between said camera and said fluid to be between about three times the height of the fluid above the height of said camera and about 1 Km;
adjusting the view in the viewfinder of said camera such that the width of the fluid is between about 1/10 and about 1/20 of the total width of the image in said viewfinder; and
positioning the aperture of said camera such that the sun is behind said aperture for all said photographs.

21. The method of claim 20 in which said fluid is a smoke plume from a smoke stack, said method further comprising selecting a sampling area for said smoke plume to be about one diameter of said smoke stack above the top of said smoke stack.

22. A system for obtaining an accurate quantitative measure of the opacity of a fluid, comprising:
at least one calibrated image receiving device,
wherein each said image receiving device is specifically calibrated to yield at least one response curve;
images taken of said fluid to include at least one mostly uniform background associated with said fluid, said images obtained with said calibrated image receiving device;
at least one algorithm implemented in software contained on computer readable medium;

at least one processor for receiving and processing said images and implementing said software to facilitate analyzing said processed images to obtain said measure of opacity, wherein said opacity may be measured under various ambient conditions, including measurement at night, and wherein said opacity may be measured under said various ambient conditions without need for operator interpretation.

23. The system of claim 22 in which said fluid is at least one airborne fluid.

24. The system of claim 22 in which said fluid comprises at least one airborne effluent selected from the group consisting of: point source effluents, non-point source effluents, exhaust plumes, smoke, dust, and combinations thereof.

25. The system of claim 22 in which said fluid is at least one liquid.

26. The system of claim 22 in which said imaging receiving device is at least one camera.

27. The system of claim 22 in which said image receiving device is at least one digital camera,
wherein at least one of said digital cameras incorporates manual exposure control.

28. The system of claim 22 in which said images are photographs.

29. The system of claim 22 in which said images are digital photographs taken in the visible light spectrum.

30. The system of claim 22 in which said background is selected from the group consisting of: naturally occurring backgrounds, man made backgrounds, pre-specified man made backgrounds, and combinations thereof.

31. The system of claim 22 in which said software is selected from the group consisting of: Commercial-off-the-shelf (COTS) software, commercially available software, application specific software, custom software, shareware, freeware, and combinations thereof.

32. The system of claim 22 in which said processors are selected from the group consisting of: personal computers, computers, application specific integrated circuits (ASICs), personal digital assistants (PDAs), laptop computers, digital processors, and combinations thereof.

33. The system of claim 22 further comprising at least one source of energy in the visible light spectrum,
wherein, under pre-specified conditions of ambient lighting, said source illuminates said fluid.

34. The system of claim 22 further comprising at least one source of energy in the visible light spectrum,
wherein, under pre-specified conditions of ambient lighting, said source illuminates at least one artificial background associated with said fluid.

35. An instrument package for receiving images used as input for analysis leading to an accurate quantitative measure of the opacity of a fluid, said package comprising at least one calibrated image receiving device and means for performing at least part of said analysis,
wherein each said image receiving device is specifically calibrated to yield at least one response curve; and
wherein said opacity may be measured under various ambient conditions, including measurement at night, and
wherein said opacity may be measured under said various ambient conditions without operator interpretation.

36. The instrument package of claim 35 in which said image receiving device is at least one digital camera,
wherein at least one of said digital cameras incorporates manual exposure control.

37. The instrument package of claim 35 said means for performing at least part of said analysis further comprising at least one processor selected from the group consisting of: personal computers, computers, application specific integrated circuits (ASICs), personal digital assistants (PDAs), laptop computers, digital processors, and combinations thereof.

38. The instrument package of claim 35 further comprising software contained on computer readable media, said software selected from the group consisting of: Commercial-off-the-shelf (COTS) software, commercially available software, application specific software, custom software, shareware, freeware, and combinations thereof.

39. The instrument package of claim 35 further comprising at least one source of energy in the visible light spectrum,
wherein, under pre-specified conditions of ambient lighting, said source illuminates said fluid.

40. The instrument package of claim 35 further comprising at least one source of energy in the visible light spectrum,
wherein, under pre-specified conditions of ambient lighting, said source illuminates at least one artificial background associated with said fluid.

41. A system for obtaining an accurate quantitative measure of the opacity of a fluid, comprising:
at least one calibrated means for receiving images,
wherein each said means for receiving images is specifically calibrated to yield at least one response curve;
images of said fluid to include at least one background associated with said fluid, said images obtained with said image receiving device;
at least one means for processing said images as received from said calibrated means; and
means for implementing at least one algorithm on said means for processing to analyze said images to obtain said measure of opacity,
wherein said opacity may be measured under various ambient conditions, including measurement at night, and
wherein said opacity may be measured under said various ambient conditions without need for operator interpretation.

42. The system of claim 41 further comprising means for illuminating in the visible light spectrum,
wherein, under pre-specified conditions of ambient lighting, said means for illuminating is employed to illuminate said fluid.

43. The system of claim 41 further comprising means for illuminating in the visible light spectrum,
wherein, under pre-specified conditions of ambient lighting, said means for illuminating is employed to illuminate at least one artificial background associated with said fluid.

44. The system of claim 41 in which:
said calibrated means for receiving images is at least one specifically calibrated digital camera;
said images are digital photographs;
said backgrounds are selected from the group consisting of: naturally occurring backgrounds, man made backgrounds, pre-specified man made backgrounds, and combinations thereof;
said means for processing data are selected from the group consisting of: personal computers, computers, application specific integrated circuits (ASICs), personal digital assistants (PDAs), laptop computers, digital processors, and combinations thereof;
said means for implementing said algorithms are selected from the group consisting of: Commercial-off-the-shelf (COTS) software, commercially available software, application specific software, custom software, shareware, freeware, and combinations thereof, and
said means for illuminating comprise at least one source of energy in the visible light spectrum.

45. A method for obtaining an accurate quantitative measure of the opacity of a fluid at night or in low ambient light conditions, comprising:
   illuminating said fluid with energy in the visible light spectrum;
   providing at least one image receiving device incorporating at least one light sensitive device;
   specifically calibrating said image receiving devices,
wherein said calibrating yields at least one response curve for each said image receiving device;
   employing at least one said image receiving device for taking images of said fluid, said images to include at least one background associated with said fluid;
   providing at least one algorithm; implemented in software contained on computer readable media;
   providing at least one processor for at least running said software;
   receiving and processing said image on at least one said processor; and
   analyzing said image using said algorithm and said software to obtain said measure of opacity,
wherein said opacity may be measured under various ambient conditions, including measurement at night, and
wherein said opacity may be measured under said various ambient conditions without operator interpretation.

46. The method of claim 45 illuminating said fluid with at least one artificial source of light oriented toward said fluid and located approximately on-axis of a line between said fluid and said image receiving device,
wherein said source is closer to said fluid than to said image receiving device.

47. The method of claim 45 illuminating said fluid with at least one artificial source of light oriented toward said fluid and located off-axis from the orientation of said image receiving device to said fluid,
wherein said source of light is closer to said fluid than to said image receiving device.

48. The method of claim 45 illuminating said fluid with at least one artificial source of light oriented toward said fluid and located approximately on-axis of a line between said fluid and said image receiving device, said fluid located between said source and said image receiving device,
wherein said source of light is closer to said fluid than said image receiving device is to said fluid.

49. The method of claim 45, said algorithm comprising:

$$O = \frac{\frac{I}{I_{SKY}} - 1}{\frac{J}{I_{SKY}} - 1}$$

wherein, $$\frac{I}{I_{SKY}}$$

is determined from a photograph using a technique for calibrating digital cameras comprising:
   empirically obtaining a response curve for at least one type of digital camera having a minimum resolution of approximately one megapixel and employing a charge coupled device (CCD) by:
      fixing the aperture of said camera at a pre-specified value to minimize vignetting;
      setting the sensitivity factor of said CCD at a pre-specified value,
wherein exposure is dependent upon only two variables, scene radiance, I, and exposure time, T;
      selecting a homogeneous background suitable for diffusing at least energy in the visible light spectrum impinging thereon,
      wherein an average of pixel values, $PV_{AVE}$, may be used to represent mean scene radiance, and
      wherein homogeneous incident radiance is assumed over the area of the aperture of said camera;
      taking photographs of said background,
      wherein said photographs are taken during a pre-specified time interval, and
      wherein during each said interval said photographs are acquired using multiple different exposure times, and
      wherein lighting conditions are stable to ensure constant scene radiance;
      cropping each said photograph to employ the center of each;
      determining $PV_{AVE}$ from said cropped photographs;
      multiplying the square of the aperture diameter, A, by the exposure time, T, for each said cropped photograph;

$$\text{plotting } \ln(PV) \text{ versus } \ln\left(\frac{A^2 T}{A_{\min}^2 T_{\min}}\right),$$

wherein $A_{min}$ is the minimum aperture diameter setting and $T_{min}$ is the minimum exposure time used for said set of said photographs;
      determining and plotting as a first curve a first set of data for ln(PV) vs. ln($A^2T$)' from said digital images taken at a first level of radiance to yield incidence value, $I_1$;
      determining and plotting as a second curve, approximately parallel to said first curve, a second set of data for ln(PV) vs. ln($A^2T$)' from said digital images taken at a second level of radiance to yield incidence value, $I_2$,
      wherein the relationships described by ln(PV) vs. ln($A^2T$) and obtained at different radiance values are parallel to each other, each point being obtained from one said digital photograph of said background, and
      wherein said first and second curves are polynomial regression lines for said first and second sets of data, and
      wherein a constant vertical distance between said two curves represents the constant ratio of the radiance values, ln($I_1/I_2$), and
      wherein, $$\frac{J}{I_{SKY}}$$

is determined practically from a photograph with known opacity, such that for a photograph indicating 50% opacity, the radiance ratio between said fluid and sky, $$\frac{I_{P50\%}}{I_{SKY}}$$

is determined by means of a camera response function obtained during said calibration, such that the calibrated value for $$\frac{J}{I_{SKY}}$$

is $$\frac{1}{0.5}\left(\frac{I_{P50\%}}{I_{SKY}} - 1\right) + 1.$$

* * * * *